United States Patent
Last et al.

(10) Patent No.: US 9,056,948 B2
(45) Date of Patent: *Jun. 16, 2015

(54) MICROCAPSULES AND PRODUCTION THEREOF

(75) Inventors: Klaus Last, Osterode (DE); Daniel Mues, Leese (DE)

(73) Assignee: FOLLMANN & CO. GESELLSCHAFT FUER CHEMIE-WERKSTOFFE UND VERFAHRENSTECHNIK MBH & CO. KG, Minden (DE)

( * ) Notice: Subject to any disclaimer, the term of this patent is extended or adjusted under 35 U.S.C. 154(b) by 140 days.

This patent is subject to a terminal disclaimer.

(21) Appl. No.: 13/634,107

(22) PCT Filed: Mar. 14, 2011

(86) PCT No.: PCT/EP2011/001253
§ 371 (c)(1),
(2), (4) Date: Nov. 21, 2012

(87) PCT Pub. No.: WO2011/110368
PCT Pub. Date: Sep. 15, 2011

(65) Prior Publication Data
US 2013/0137626 A1    May 30, 2013

(30) Foreign Application Priority Data

Mar. 12, 2010   (EP) .................. PCT/EP2010/001572
Sep. 13, 2010   (EP) ..................................... 10009497

(51) Int. Cl.
| | |
|---|---|
| *C08G 73/06* | (2006.01) |
| *A01N 25/28* | (2006.01) |
| *A61K 9/50* | (2006.01) |
| *B01J 13/14* | (2006.01) |
| *B01J 13/20* | (2006.01) |
| *C09B 67/02* | (2006.01) |
| *C11D 3/50* | (2006.01) |
| *C11D 17/00* | (2006.01) |
| *F28D 20/02* | (2006.01) |
| *C08G 12/32* | (2006.01) |

(52) U.S. Cl.
CPC ............ *C08G 73/0644* (2013.01); *A01N 25/28* (2013.01); *A61K 9/5026* (2013.01); *A61K 9/5031* (2013.01); *A61K 9/5073* (2013.01); *A61K 2800/412* (2013.01); *B01J 13/14* (2013.01); *B01J 13/203* (2013.01); *B01J 13/206* (2013.01); *C09B 67/0097* (2013.01); *C11D 3/505* (2013.01); *C11D 17/0039* (2013.01); *F28D 20/023* (2013.01); *C08G 12/32* (2013.01); *Y02E 60/145* (2013.01)

(58) Field of Classification Search
CPC ............................ C08G 73/0644; C08G 12/32
USPC ........................................................... 512/4
See application file for complete search history.

(56) References Cited

U.S. PATENT DOCUMENTS

| | | |
|---|---|---|
| 3,576,660 A | 4/1971 | Bayless et al. |
| 3,755,190 A | 8/1973 | Hart et al. |
| 4,406,816 A | 9/1983 | Sliwka |
| 4,525,520 A * | 6/1985 | Shioi et al. .................... 524/512 |
| 4,601,863 A | 7/1986 | Shioi et al. |
| 4,880,721 A | 11/1989 | Ishikawa |
| 4,898,696 A | 2/1990 | Sliwka |
| 4,918,317 A | 4/1990 | Hess et al. |
| 4,936,916 A | 6/1990 | Shinmitsu et al. |
| 5,162,486 A | 11/1992 | Follmann et al. |
| 5,422,176 A | 6/1995 | Schuler et al. |
| 6,224,795 B1 | 5/2001 | Frank et al. |
| 6,261,483 B1 | 7/2001 | Frank et al. |
| 6,380,137 B1 | 4/2002 | Heier et al. |
| 6,682,750 B2 | 1/2004 | Loeffler et al. |
| 6,719,931 B2 | 4/2004 | Hoffman et al. |
| 2003/0004226 A1 | 1/2003 | Hoffman et al. |
| 2006/0165639 A1 | 7/2006 | Gauweiler et al. |
| 2007/0138672 A1 | 6/2007 | Lee et al. |
| 2008/0169006 A1 | 7/2008 | Musale et al. |
| 2012/0122694 A1 | 5/2012 | Last et al. |

FOREIGN PATENT DOCUMENTS

| | | |
|---|---|---|
| CA | 882175 A | 9/1971 |
| CA | 1104881 A1 | 7/1981 |

(Continued)

OTHER PUBLICATIONS

International Search Report, dated Oct. 11, 2011.
Bouhamed H. et al. "Alumina interaction with AMPS-MPEG random copolymers", Journal of Collod and Interface Science, Academic Press, New York, US, Bd. 261, Nr. 2, May 15, 2003, p. 264-272 SP027457372.

*Primary Examiner* — Ling Choi
*Assistant Examiner* — Lanee Reuther
(74) *Attorney, Agent, or Firm* — Norman B. Thot

(57) ABSTRACT

The invention relates to microcapsules, the capsule walls of which comprise a resin that can be obtained by reacting a) at least one compound selected from the group consisting of a1) amines and a2) aromatic or heteroaromatic compounds which are unsubstituted or substituted with one or more substituents from the group consisting of $C_1$-$C_{20}$-alkyl, OH, OR, COOH, SH, SR, NHCOR, OCOR, halogen, or an aromatic compound, where R is a $C_1$-$C_{10}$-alkyl group, with b) at least one aldehydic component that contains at least two carbons atoms per molecule, in the presence of c) at least one copolymer which contains units of 2-acrylamido-2-methylpropane sulphonic acid or salts (AMPS) thereof and/or 2-acrylamido-2-methylpropane phosphonic acid or salts (AMPP) thereof and units of one or more (meth)acrylates.

28 Claims, No Drawings

(56) References Cited

FOREIGN PATENT DOCUMENTS

| | | |
|---|---|---|
| CA | 2 090 343 C | 9/1993 |
| DE | 3814250 A1 | 11/1988 |
| DE | 19833347 A1 | 1/2000 |
| DE | 19835114 A1 | 2/2000 |
| EP | 0026914 A1 | 4/1981 |
| EP | 0120504 A1 | 10/1984 |
| EP | 0152083 A2 | 8/1985 |
| EP | 0218887 A2 | 4/1987 |
| EP | 0319337 A1 | 6/1989 |
| EP | 0383358 A2 | 8/1990 |
| EP | 0415273 A2 | 3/1991 |
| EP | 0978312 A1 | 2/2000 |
| EP | 1033378 A1 | 9/2000 |
| EP | 1236464 A2 | 9/2002 |
| EP | 1797946 A2 | 6/2007 |
| GB | 1 603 448 | 11/1981 |
| JP | 54-17377 A | 2/1979 |
| JP | 6-361 A | 1/1994 |
| JP | 6-172458 A | 6/1994 |
| JP | 6-312128 A | 11/1994 |
| JP | 2003-519724 A | 6/2003 |
| JP | 2006-501255 A | 1/2006 |
| JP | 2012-520165 A | 9/2012 |
| WO | WO 01/51197 A1 | 7/2001 |
| WO | WO 2006/032019 A1 | 3/2006 |
| WO | WO 2010/102830 A2 | 9/2010 |

* cited by examiner

MICROCAPSULES AND PRODUCTION THEREOF

CROSS-REFERENCES TO RELATED APPLICATIONS

This application is the U.S. National Stage of International Application No. PCT/EP2011/001253, filed Mar. 14, 2011, which designated the United States and has been published as International Publication No. WO 2011/110368 A2 and which claims the priority of EP Patent Application, Serial No. 10 009 497.8, filed Sep. 13, 2010, pursuant to 35 U.S.C. 119(a)-(d).

BACKGROUND OF THE INVENTION

The invention relates to microcapsules whose capsule walls comprise a resin which is obtainable by reacting at least one amine and/or defined aromatics or heteroaromatics and at least one aldehydic component which has at least two C atoms per molecule in the presence of at least one copolymer which comprises units of AMPS and/or AMPP and (meth)acrylates, and also to dispersions comprising such microcapsules. Additionally provided by the invention are the use and the production of the microcapsules/microcapsule dispersions, and also products which comprise such microcapsules/microcapsule dispersions, and the use thereof.

From the prior art, microcapsules are known which may comprise liquid, solid or gaseous substances as core material. Commonplace materials for the capsule walls are, for example, phenol-formaldehyde polymers, melamine-formaldehyde polymers, polyurethane, gelatin, polyamides or polyureas. Widespread, for example, is the use of microcapsules filled with leuco dye for the production of carbonless copy papers.

From U.S. Pat. No. 3,755,190 it is known that capsules made of phenol-formaldehyde polymers have fragile walls. In order to avoid this, a production method is described in which fully hydrolyzed polyvinyl alcohol is used.

Dispersions of microcapsules made from aminoplast resins, such as melamine-formaldehyde resins, inevitably contain—as a result of their production—a certain fraction of free formaldehyde. For environmental and workplace safety reasons it is desirable to minimize the formaldehyde content, and if possible to avoid formaldehyde entirely.

For the purpose of reducing the formaldehyde content it is customary to add formaldehyde scavengers to microcapsule dispersions based on melamine-formaldehyde resins. The formaldehyde scavengers most frequently used include ammonia, urea, ethyleneurea, and melamine, which reduce the residual formaldehyde content of the capsule dispersion.

EP-A 0 383 358 and DE-A 38 14 250 disclose light-sensitive materials consisting of microcapsules whose walls are formed from melamine-formaldehyde resins. Urea is added in the course of curing, for the purpose of removing excess formaldehyde.

In the case of the methods described in EP-A 319 337 and U.S. Pat. No. 4,918,317, urea is added toward the end of curing.

EP-A 0 415 273 describes the production and use of monodisperse and polydisperse solid-sphere particles made of melamine-formaldehyde condensate. To bind the formaldehyde released during the condensation, the use of ammonia, urea or ethyleneurea is proposed.

Microcapsules made of melamine-formaldehyde resins produced using polymers containing sulfonic acid groups are notable for their uniform capsule size and imperviousness (EP-A 0 218 887 and EP-A 0 026 914). These capsule dispersions, however, still contain residual free formaldehyde, whose presence is unwanted during further processing.

EP-A 0 026 914 therefore recommends binding the formaldehyde, following curing, using ethyleneurea and/or melamine as formaldehyde scavengers.

Known from DE 198 35 114 are dispersions of microcapsules based on melamine-formaldehyde resin, the melamine-formaldehyde resin being partially etherified and comprising a water-soluble primary, secondary or tertiary amine or ammonia. Prior to curing, urea is added as a formaldehyde scavenger.

DE 198 33 347 describes a method for producing microcapsules by condensation of melamine-formaldehyde resins and/or their methyl ethers, where urea or urea whose amino groups are joined with an ethylene or propylene bridge is added as a formaldehyde scavenger prior to curing. The resulting dispersions are indeed low in formaldehyde, but the addition of urea prior to curing adversely affects the stability of the microcapsules and the viscosity of the microcapsule dispersion.

WO 01/51197 teaches a method for producing microcapsules by condensation of melamine-formaldehyde resins, where a mixture of melamine and urea is added in the course of curing.

The addition of the stated formaldehyde scavengers to the completed microcapsule dispersion or during the production of the microcapsule dispersion generally lowers the formaldehyde content of the dispersion. Often, however, it is not possible to reduce below a defined limit the formaldehyde content of products which comprise such microcapsule dispersions or have been treated with such microcapsule dispersions, even when large amounts of formaldehyde scavengers are added.

SUMMARY OF THE INVENTION

It is an object of the present invention, therefore, to develop microcapsules having an extremely low formaldehyde content and/or, preferably, to forgo entirely the use of formaldehyde for microcapsules.

DETAILED DESCRIPTION OF PREFERRED EMBODIMENTS

This object is achieved by the microcapsules of the invention, whose capsule walls comprise a resin which is obtainable by reacting
a) at least one compound selected from the group of
b) a1) amines and
c) a2) aromatic or heteroaromatic compounds which are unsubstituted or substituted by one or more substituents from group $C_1$-$C_{20}$ alkyl, OH, OR, COOH, SH, SR, NHCOR, OCOR, halogen (F, Cl, Br, I), $C_6$-$C_{14}$ aryl such as unsubstituted or substituted phenyl or naphthyl (in each case for example substituted by $C_1$-$C_{10}$ alkyl, $C_1$-$C_{10}$ alkoxy, halogen, halo-$C_1$-$C_{10}$ alkyl, or halo-$C_1$-$C_{10}$ alkoxy), where R represents a $C_1$-$C_{10}$ alkyl group,
d) with
at least one aldehydic component which has at least two C atoms per molecule, in the presence
of at least one copolymer which comprises units of 2-acrylamido-2-methylpropanesulfonic acid or its salts (AMPS) and/or 2-acrylamido-2-methylpropanephosphonic acid or its salts (AMPP) and units of one or more (meth)acrylates.

The invention further relates to microcapsule dispersions comprising such microcapsules of the invention.

Surprisingly it is possible in accordance with the invention to produce stable core-shell microcapsules featuring high chemical and physical resistance, which satisfy the requirements and feasibility of industrial manufacture (scale-up).

In this context it is possible to produce in situ, from the building blocks a) and b), precondensates which can also be used further directly in a one-pot process to give oil-in-water or water-in-oil microencapsulations.

The invention further provides a method for producing microcapsules and microcapsule dispersions of the invention, wherein a) at least one compound selected from the group of the amines a1) and/or the aromatic or heteroaromatic compounds a2) such as aromatic or heteroaromatic alcohols (or ethers or derivatives thereof) and/or aromatic or heteroaromatic carboxylic acids (or esters thereof) and b) the at least one aldehydic component which has at least two C atoms per molecule, are combined and reacted in the presence c) of at least one copolymer which comprises units of AMPS and/or AMPP and one or more (meth)acrylates, and later the curing of the capsules takes place.

The production of such microcapsule dispersions is achieved via the use of suitable precondensates but also in situ in a one-pot process.

In the definition of component a), the aromatic or heteroaromatic compounds a2) are different from amines; the compounds a2) therefore do not include amines a1). As component a), it is possible to use one or more (e.g., two, three or four) compounds, preferably one compound, from the groups a1) and/or a2). There may be, for example, one or more (e.g., two, three or four) amines a1) or one or more (e.g., two, three or four) aromatic or heteroaromatic compounds a2). Preferred compounds a2) are aromatic or heteroaromatic alcohols (or their ethers and esters) and/or one or more (e.g., two, three or four) aromatic or heteroaromatic carboxylic acids (or their esters); particularly preferred compounds a2) are aromatic alcohols (or their ethers and esters).

If two or more (e.g., two, three or four) compounds a) are used, it is possible to use two or more compounds a1), two or more compounds a2), or two or more compounds from different subgroups a1) or a2), as for example one or more (e.g., two) compounds a1), one or more (e.g., two) compounds a2), or one or more (e.g., two) compounds a1) and one or more (e.g., two) compounds a2), as for example an amine and an aromatic alcohol such as urea-resorcinol, urea-phloroglucinol, melamine-resorcinol or melamine-phloroglucinol. Hence the present invention opens up a multiplicity of thermoset-based wall materials which are formaldehyde-free and can be tailored specifically to the particular profiles of requirements of the industrial application.

As component a) it is preferred to use just one compound, preferably an amine a1) or an aromatic or heteroaromatic compound a2) such as an aromatic alcohol.

Particularly preferred as component a) are the amines a1), optionally in combination with compounds a2).

Amines a1) used in the context of the present invention are, for example, acyclic, aromatic or heteroaromatic, preferably acyclic or heteroaromatic, amines. The amines may have one or more amine groups. The amines preferably have two or more amine groups, more particularly two or three amine groups. Further preferred are amines having at least one amine function which has at least one hydrogen atom. Primary and secondary amines are preferred. Particularly preferred are amines having two or three amino functions which constitute primary or secondary amine functions. Especially preferred are amines which have two or three primary amino functions. Further preferred are amines which form Schiff bases, imines or enamines in the reaction with aldehydes b).

The following compounds, for example, are contemplated as amines a1) in accordance with the invention:

$C_1$-$C_{20}$ alkylamines such as 1,2-diaminohexane, 1,3-diaminohexane, 1,2-diaminodecane, 1,3,5-triaminoeicosane, ureas such as urea, methylurea, dimethylurea, methylolureas, which may be partly or wholly etherified or esterified, such as methylolurea, dimethylolurea and di(methylmethylol)urea, thioureas such as thiourea, methylthiourea, dimethylthiourea, methylolthioureas, which may be partly or wholly etherified or esterified, such as methylolthiourea, dimethylolthiourea, and di(methylmethylol)thiourea, triazines such as melamines, e.g., melamine, methylolmelamines, which may be partly or wholly etherified or esterified, such as hexamethylolmelamine or methylated hexamethylolmelamine, imino-melamines, e.g., iminomelamine, guanidines, e.g., guanidine; benzylguanidine and guanidine carbonate, guanines, e.g., guanine, uracils, e.g., uracil, thymines, e.g., thymine, cytosines, e.g., cytosine, adenines, e.g., adenine, benzoguanamines, e.g., benzoguanamine, acetoguanamine, benzotriazoles, e.g., benzotriazole, glycourils, e.g., glycouril, indoles, e.g., indole and indoles substituted by primary or secondary amine groups, pyrrols, e.g., pyrrole and pyrroles substituted by primary or secondary amine groups, pyridines, e.g., pyridine and pyridines substituted by primary or secondary amine groups, pyrimidines, e.g., pyrimidine, and pyrimidines substituted by primary or secondary amine groups, such as alpha-aminopyrimidine, pyrazines, e.g., pyrazine and pyrazines substituted by primary or secondary amine groups, quinolines, e.g., quinoline and quinolines substituted by primary or secondary amine groups.

The aforementioned aromatic or heteroaromatic amines may also carry additionally the following substituents, for example, as well as amino functions, on the cyclic parent structure: $C_1$-$C_{20}$ alkyl, OH, OR, SH, SR, COOH, NHCOR, OCOR, $SO_3H$, $PO_3H$, halogen (F, Cl, Br, I), $C_6$-$C_{14}$ aryl such as unsubstituted or substituted phenyl or naphthyl (e.g., substituted by $C_1$-$C_{10}$ alkyl, $C_1$-$C_{10}$ alkoxy, halogen, halo-$C_1$-$C_{10}$ alkyl or halo-$C_1$-$C_{10}$ alkoxy), where R represents a $C_1$-$C_{20}$ alkyl group and the groups OH, SH, COOH, $SO_3H$, and $PO_3H$ may also be present in the form of their salts.

In the reaction of amine component and aldehydes, the molar ratio between nitrogen-bonded hydrogen atoms and aldehyde functions is generally between 0.01 and 1:1, preferably between 0.2 and 1:1. Through a suitable choice of the reactivities of the components employed, the reaction products afford the possibility of custom-tailoring the rate of formation of the wall material needed for forming the capsule wall, the network density, the wall thickness, and the nature of the thermoset wall material to the requirements.

Preferred components a1) are ureas, melamines, and benzoguanamines and mixtures thereof. Particularly preferred components a1) are urea, melamine, and benzoguanamine, and mixtures thereof, very preferably urea, melamine, and urea/melamine.

The amino resin condensates are produced in accordance with the techniques customary for the production of aminoplast condensates. Reaction of aldehydes b) with a1) components produces polycondensates which have OH groups in alpha-position to amine moieties.

The appropriate reaction temperature for producing the amino resin products from amine a1) and aldehyde is generally between 20° C. and 90° C., preferably between 40° C. and 60° C., at pH levels in general between 2 and 10.

The reaction can be carried out in aqueous phase or in organic phase. Suitable solvents are water, alcohols, aromatic or aliphatic hydrocarbons such as mineral oils, for example, myristates, etc. Reaction in aqueous phase is particularly preferred.

Also suitable as component a) are aromatic and heteroaromatic compounds a2). These compounds are able to enter into an electrophilic reaction with the aldehyde component, and subsequently allow polycondensation reactions.

Examples of aromatic and heteroaromatic compounds a2) are unsubstituted aromatic and heteroaromatic compounds such as indene, benzene, and toluene.

Compounds a2) of preferential suitability are substituted aromatic and heteroaromatic compounds.

Preferred in this context are aryloxyalkanols, arylalkanols, and oligoalkanol aryl ethers; also suitable are compounds which provide electron-rich double bonds, examples being enol ethers or enamine systems such as benzofuran, furan, and pyran.

Particularly preferred compounds a2) are aromatic alcohols and ethers thereof or derivatives thereof, preferred derivatives being esters.

Especially preferred are aromatic and heteroaromatic, preferably aromatic, compounds in which at least one free hydroxyl group or carboxylic acid group, more preferably at least two free hydroxyl or carboxylic acid groups, are bonded directly on the aromatic or heteroaromatic ring. It is particularly preferred in this case if at least two free hydroxyl groups or carboxylic acid groups are bonded directly to an aromatic ring, and very preferably are located in meta-position to one another. It is further preferred for the aromatic alcohols and carboxylic acids to be selected from phenols, cresols (o-, m-, and p-cresol), naphthols (α- and β-naphthol), and thymol, and also from ethylphenols, propylphenols, fluorophenols, and methoxyphenols, and also trimesic acid and its esters, gallic acid and its esters, terephthalic acid and its esters, phthalic acid and its esters, and phthalic anhydride, and also mixtures thereof. The alcohols and carboxylic acids may also be present in the form of their salts, as alkoxide or carboxylate, respectively.

Aromatic alcohols preferred in accordance with the invention are also those which are used in the production of polycarbonate plastics (e.g., for compact discs, plastic dishes, baby bottles) and epoxy resin varnishes (e.g., for coatings on preserve cans and film packaging), more particularly 2,2-bis(4-hydroxyphenyl)propane (bisphenol A).

It is especially preferred if an aromatic alcohol is selected from the phenols having two or more hydroxyl groups, preferably from 2,2-bis(4-hydroxyphenyl)propane (bisphenol A), pyrocatechol, resorcinol, hydroquinone and 1,4-naphthohydroquinone, phloroglucinol, pyrogallol, and hydroxyhydroquinone, with resorcinol and/or phloroglucinol more particularly being preferred as aromatic alcohols.

In one embodiment, the microcapsules of the invention are obtained by using the aromatic alcohol in the form of an ether, the ether, in one preferred embodiment, being a derivative of the respective free form of the aromatic alcohol for reaction in accordance with the invention. The free alcohol may also be present here; in that case, accordingly, there is a mixture. For this instance, the molar ratio between the free form of the aromatic alcohol for reaction in accordance with the invention and the stated additional component (ether form of an aromatic alcohol) may be between 0:100, preferably, preferably 1:1, or 1:2 or 1:4.

The reason for the advantage of the mixture of the aromatic alcohol with an ether form is that thereby it is possible to influence the reactivity of the system. With the suitable selection of the ratio it is possible more particularly to create a system whose reactivity is in a balanced proportion with the storage stability of the system.

Preferred esters of the aromatic alcohols are those which do not enter into any secondary reactions under the polycondensation conditions and which possess sufficient reactivity, for the electrophilic attack of the aliphatic and aromatic aldehydes used, to generate polycondensation products in a high yield. Of particular interest are, more particularly, the esters of carboxylic acids, sulfonic acids, phosphoric acids, and phosphonic acids, but also those which possess an interface activity which can be adjusted with relatively long carbon chains.

Examples of suitable ester groups include saturated or unsaturated, straight-chain, branched or cyclic hydrocarbon radicals, which may contain one or more heteroatoms such as N, O, S, P, F, Cl, Br or I, examples being the esters of formic acid and salts thereof, acetic acid and salts thereof, propionic acid and salts thereof, and also esters of $C_6$-$C_{14}$ carboxylic acids and salts thereof, sulfonic esters, e.g., para-toluenesulfonic esters, amidosulfonic esters, and phosphoric esters, all based on the abovementioned aromatic and heteroaromatic alcohols and carboxylic acids.

In this description, the term "aromatic" (alone or in conjunction with other terms) identifies a monocyclic or polycyclic (e.g., 2 or 3 rings) aromatic ring system, preferably having 6 to 14 ring atoms, e.g., benzene or naphthalene. The term "heteroaromatic" (alone or in conjunction with other terms) identifies an aromatic heterocyclic ring system, preferably having 5 to 14 ring atoms. The heteroaromatic may be monocyclic or polycyclic (e.g., 2 or 3 rings). Examples of heteroaromatic amines a1) are indole, pyrole, pyridine, pyrimidine, pyrazine, triazine, and quinoline. Examples of heteroaromatic compounds a2) are furan, benzofuran, thiophene, benzothiophene, pyran, and benzopyran.

Aldehydes b) having at least 2 C atoms that are preferred in accordance with the present invention include not only aliphatic but also aromatic aldehydes. As aldehydic component b) it is also possible to use aldehyde precursors (latent aldehydes), such as acetals and hemiacetals.

Particularly preferred aldehydes are one or more selected from the following group: valeraldehyde, caproaldehyde, caprylaldehyde, decanal, succinaldehyde, cyclohexanecarbaldehyde, cyclopentanecarbaldehyde, 2-methyl-1-propanal, 2-methylpropionaldehyde, acetaldehyde, acrolein, aldosterone, antimycin A, 8'-apo-β-caroten-8'-al, benzaldehyde, butanal, chloral, citral, citronellal, crotonaldehyde, dimethylaminobenzaldehyde, folic acid, fosmidomycin, furfural, glutaraldehyde, glyceraldehyde, glycolaldehyde, glyoxal, glyoxylic acid, heptanal, 2-hydroxybenzaldehyde, 3-hydroxybutanal, hydroxymethylfurfural, 4-hydroxynonenal, isobutanal, isobutyraldehyde, methacrolein, 2-methylundecanal, mucochloric acid, N-methylformamide, 2-nitrobenzaldehyde, nonanal, octanal, oleocanthal, orlistat, pentanal, phenylethanal, phycocyanin, piperonal, propanal, propenal, protocatechualdehyde, retinal, sal icylaldehyde, secologanin, streptomycin, strophanthidin, tylosin, vanillin, and cinnamaldehyde. Preference is likewise given to the aldehyde precursors (latent aldehydes) of the aforementioned aldehydes, examples being their acetals and hemiacetals.

For the purposes of the present invention it is possible for the aldehydic component to have at least one or two, more preferably two, three or four, very preferably two free aldehyde groups per molecule, it being preferred for glyoxal, glyoxylic acid, glutaraldehyde and/or succinaldehyde to be present as aldehydic component, more particularly glyoxal, glutaraldehyde and/or succinaldehyde; glutaraldehyde is particularly preferred.

In the microcapsules of the invention, the molar ratio of a) of the at least one amine and/or aromatic or heteroaromatic compound (e.g., aromatic alcohol or ether thereof or derivative thereof such as ester) to b) the at least one aldehydic component may be generally between 1:1 and 1:5, more preferably between 1:1 and 1:3. The ratio in the case of resorcinol as component a) is preferably about 1:1.5 to 1:3, in the case of phloroglucinol about 1:1 to 1:2, in the case of melamine about 1:1.5 to 1:2, and in the case of urea about 1:1.2 to 1:1.5. The weight ratio of components a)+b) to c) (protective colloid), i.e., the ratio of the sum total weight of a)+b) to the weight of component c), is in general between 1:1 and 1:0.01, more preferably between 1:0.2 and 1:0.05.

The copolymers c) used in the context of the present invention comprise units of 2-acrylamido-2-methylpropanesulfonic acid or its salts (AMPS, commercially available for example as Lupasol® PA 140, BASF), e.g., alkali metal salts such as sodium or potassium salts or ammonium salts, e.g., 2-acrylamido-2-methylpropanesulfonic acid potassium salt, or 2-acrylamido-2-methylpropanephosphonic acid or salts thereof, e.g., alkali metal salts such as sodium or potassium salts or ammonium salts, and one or more (meth)acrylates. AMPS and AMPP may also be used in a mixture here. The term "(meth)acrylate" in this application identifies both methacrylates and acrylates. The copolymers are suitable as protective colloids and can be used advantageously during the production of microcapsules.

Particularly suitable base monomers include the following:

2-Acrylamido-2-methylpropanesulfonic acid and its alkali metal and ammonium salts

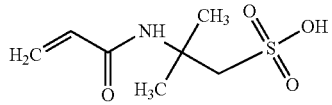

2-Acrylamido-2-methyl-1-propanephosphonic acid and its alkali metal and ammonium salts

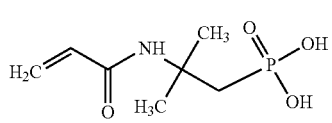

Particularly preferred are copolymers c) based on AMPS. The copolymers c) may be constructed from two or more comonomers, as for example from two comonomers (bipolymers), three comonomers (terpolymers) or from four comonomers. In addition to AMPS and/or AMPP there may be one, two or more, more particularly one or two (meth)acrylate comonomers present.

As well as AMPS and/or AMPP there are one or more (meth)acrylate monomers present and optionally one or more further monomers, examples being acrylamide, N-vinylpyrrolidone (available commercially as Luviskol® K15, K30 or K90, BASF), di- or polycarboxylates or polystyrene sulfonates, vinyl compounds such as vinyl esters, styrenes, vinyl ethers, N-vinylcaprolactam, vinylphosphoric acid and its salts and esters, vinylphosphonic acid and its salts and esters, vinylsulfonic acid and its salts and esters, vinylcarboxylic acids and their salts and esters (e.g., vinylacetic acid) and/or maleic anhydride, ethylene and/or maleic anhydride, isobutylene and/or maleic anhydride, styrene-maleic anhydride, or salts of amyl compounds or allyl compounds.

Preferred (meth)acrylate comonomers are acrylic acid and methacrylic acid and their esters, the ester groups being, for example, saturated or unsaturated, straight-chain, branched or cyclic hydrocarbon radicals, which may comprise one or more heteroatoms such as N, O, S, P, F, Cl, Br and/or I. Examples of such hydrocarbon radicals are straight-chain, branched or cyclic alkyl, straight-chain, branched or cyclic alkenyl, aryl such as phenyl or heterocyclyl such as tetrahydrofurfuryl.

Particularly preferred (meth)acrylate comonomers contemplated are as follows:
a) acrylic acid, $C_1$-$C_{14}$ alkyl-acrylic acid such as methacrylic acid;
b) (meth)acrylamides such as acrylamide, methacrylamide, diacetoneacrylamide, diacetonemethacrylamide, N-butoxymethylacrylamide, N-isobutoxymethylacrylamide, N-butoxymethylmethacrylamide, N-isobutoxymethylmethacrylamide, N-methylolacrylamide, N-methylolmethacrylamide;
c) heterocyclyl(meth)acrylates such as tetrahydrofurfuryl acrylate and tetrahydrofurfuryl methacrylate, or carbocyclic(meth)acrylates such as isobornyl acrylate and isobornyl methacrylate;
d) urethane(meth)acrylates such as diurethane diacrylate and diurethane methacrylate (CAS: 72869-86-4);
e) $C_1$-$C_{14}$ alkyl acrylates such as methyl, ethyl, n-propyl, isopropyl, n-butyl, sec-butyl, isobutyl, tert-butyl, n-pentyl, isopentyl, hexyl (e.g., n-hexyl, isohexyl or cyclohexyl), heptyl, octyl (e.g., 2-ethylhexyl), nonyl, decyl (e.g., 2-propylheptyl or isodecyl), undecyl, dodecyl, tridecyl (e.g., isotridecyl), and tetradecyl acrylate; the alkyl groups may be optionally substituted by one or more halogen atoms (e.g., fluorine, chlorine, bromine or iodine), e.g., trifluoroethyl acrylate, or by one or more amino groups, e.g., diethylaminoethyl acrylate, or by one or more alkoxy groups, such as methoxypropyl acrylate, or by one or more aryloxy groups, such as phenoxyethyl acrylate;
f) $C_2$-$C_{14}$ alkenyl acrylates such as ethenyl, n-propenyl, isopropenyl, n-butenyl, sec-butenyl, isobutenyl, tert-butenyl, n-pentenyl, isopentenyl, hexenyl (e.g., n-hexenyl, isohexenyl or cyclohexenyl), heptenyl, octenyl (e.g., 2-ethylhexenyl), nonenyl, decenyl (e.g., 2-propenylheptyl or isodecenyl), undecenyl, dodecenyl, tridecenyl (e.g., isotridecenyl), and tetradecenyl acrylate, and their epoxides such as glycidyl acrylate or aziridines such as aziridine acrylate;
g) hydroxyalkyl acrylates such as hydroxymethyl, hydroxyethyl, hydroxy-n-propyl, hydroxyisopropyl, hydroxy-n-butyl, hydroxy-sec-butyl, hydroxyisobutyl, hydroxy-tert-butyl, hydroxy-n-pentyl, hydroxyisopentyl, hydroxyhexyl (e.g., hydroxy-n-hexyl, hydroxyisohexyl or hydroxycyclohexyl), hydroxyheptyl, hydroxyoctyl (e.g., 2-ethylhexyl), hydroxynonyl, hydroxydecyl (e.g., hydroxy-2-propylheptyl or hydroxyisodecyl), hydroxyundecyl, hydroxydodecyl, hydroxytridecyl (e.g., hydroxyisotridecyl), and hydroxytetradecyl acrylate, the hydroxyl group being located preferably in terminal position (ω position) (e.g., 4-hydroxy-n-butyl acrylate) or in (ω–1) position (e.g., 2-hydroxy-n-propyl acrylate) of the alkyl radical;

h) alkylene glycol acrylates comprising one or more alkylene glycol units. Examples are i) monoalkylene glycol acrylates, such as acrylates of ethylene glycol, propylene glycol (e.g., 1,2- or 1,3-propanediol), butylene glycol (e.g., 1,2-, 1,3- or 1,4-butanediol), pentylene glycol (e.g., 1,5-pentanediol) or hexylene glycol (e.g., 1,6-hexanediol), in which the second hydroxyl group is etherified or esterified, as for example by sulfuric acid, phosphoric acid, acrylic acid or methacrylic acid, or ii) polyalkylene glycol acrylates such as polyethylene glycol acrylates, polypropylene glycol acrylates, polybutylene glycol acrylates, polypentylene glycol acrylates or polyhexylene glycol acrylates, whose second hydroxyl group may optionally be etherified or esterified, as for example by sulfuric acid, phosphoric acid, acrylic acid or methacrylic acid;

Examples of (poly)alkylene glycol units with etherified hydroxyl groups are $C_1$-$C_{14}$ alkyloxy-(poly)alkylene glycols (e.g., $C_1$-$C_{14}$ alkyloxy-(poly)alkylene glycol acrylates); examples of (poly)alkylene glycol units with esterified hydroxyl groups are sulfonium-(poly)alkylene glycols (e.g., sulfonium-(poly)alkylene glycol acrylates) and their salts, (poly)alkylene glycol diacrylates such as 1,4-butanediol diacrylate or 1,6-hexanediol diacrylate, or (poly)alkylene glycol methacrylate acrylates such as 1,4-butanediol methacrylate acrylate or 1,6-hexanediol methacrylate acrylate;

The polyalkylene glycol acrylates may carry an acrylate group (e.g., polyethylene glycol monoacrylate, polypropylene glycol monoacrylate, polybutylene glycol monoacrylate, polypentylene glycol monoacrylate or polyhexylene glycol monoacrylate) or two or more, preferably two, acrylate groups, such as polyethylene glycol diacrylate, polypropylene glycol diacrylate, polybutylene glycol diacrylate, polypentylene glycol diacrylate or polyhexylene glycol diacrylate;

The polyalkylene glycol acrylates may also comprise two or more polyalkylene glycol blocks that are different from one another, examples being blocks of polymethylene glycol and polyethylene glycol, or blocks of polyethylene glycol and polypropylene glycol;

The degree of polymerization of the polyalkylene glycol units or polyalkylene glycol blocks is generally in the range from 1 to 20, preferably in the range from 3 to 10, more preferably in the range from 3 to 6.

$C_1$-$C_{14}$ alkyl methacrylates such as methyl, ethyl, n-propyl, isopropyl, n-butyl, sec-butyl, isobutyl, tert-butyl, n-pentyl, isopentyl, hexyl (e.g., n-hexyl, isohexyl or cyclohexyl), heptyl, octyl (e.g., 2-ethylhexyl), nonyl, decyl (e.g., 2-propylheptyl or isodecyl), undecyl, dodecyl, tridecyl (e.g., isotridecyl), and tetradecyl methacrylate; the alkyl groups may be optionally substituted by one or more halogen atoms (e.g., fluorine, chlorine, bromine or iodine), e.g., trifluoroethyl methacrylate, or by one or more amino groups, e.g., diethylaminoethyl methacrylate, or by one or more alkoxy groups, such as methoxypropyl methacrylate, or by one or more aryloxy groups, such as phenoxyethyl methacrylate;

$C_2$-$C_{14}$ alkenyl methacrylates such as ethenyl, n-propenyl, isopropenyl, n-butenyl, sec-butenyl, isobutenyl, tert-butenyl, n-pentenyl, isopentenyl, hexenyl (e.g., n-hexenyl, isohexenyl or cyclohexenyl), heptenyl, octenyl (e.g., 2-ethylhexenyl), nonenyl, decenyl (e.g., 2-propylheptyl or isodecenyl), undecenyl, dodecenyl, tridecenyl (e.g., isotridecenyl), and tetradecenyl methacrylate, and their epoxides such as glycidyl methacrylate or aziridines such as aziridine methacrylate;

$C_1$-$C_{14}$ hydroxyalkyl methacrylates such as hydroxymethyl, hydroxyethyl, hydroxy-n-propyl, hydroxyisopropyl, hydroxy-n-butyl, hydroxy-sec-butyl, hydroxyisobutyl, hydroxy-tert-butyl, hydroxy-n-pentyl, hydroxyisopentyl, hydroxyhexyl (e.g., hydroxy-n-hexyl, hydroxyisohexyl or hydroxycyclohexyl), hydroxyheptyl, hydroxyoctyl (e.g., 2-ethylhexyl), hydroxynonyl, hydroxydecyl (e.g., hydroxy-2-propylheptyl or hydroxyisodecyl), hydroxyundecyl, hydroxydodecyl, hydroxytridecyl (e.g., hydroxyisotridecyl), and hydroxytetradecyl methacrylate, the hydroxyl group being located preferably in terminal position (ω position) (e.g., 4-hydroxy-n-butyl methacrylate) or in (ω–1) position (e.g., 2-hydroxy-n-propyl methacrylate) of the alkyl radical;

alkylene glycol methacrylates comprising one or more alkylene glycol units. Examples are i) monoalkylene glycol methacrylates, such as methacrylates of ethylene glycol, propylene glycol (e.g., 1,2- or 1,3-propanediol), butylene glycol (e.g., 1,2-, 1,3- or 1,4-butanediol), pentylene glycol (e.g., 1,5-pentanediol) or hexylene glycol (e.g., 1,6-hexanediol), in which the second hydroxyl group is etherified or esterified, as for example by sulfuric acid, phosphoric acid, acrylic acid or methacrylic acid, or ii) polyalkylene glycol methacrylates such as polyethylene glycol methacrylates, polypropylene glycol methacrylates, polybutylene glycol methacrylates, polypentylene glycol methacrylates or polyhexylene glycol methacrylates, whose second hydroxyl group may optionally be etherified or esterified, as for example by sulfuric acid, phosphoric acid, acrylic acid or methacrylic acid;

Examples of (poly)alkylene glycol units with etherified hydroxyl groups are $C_1$-$C_{14}$ alkyloxy-(poly)alkylene glycols (e.g., $C_1$-$C_{14}$ alkyloxy-(poly)alkylene glycol methacrylates), examples of (poly)alkylene glycol units with esterified hydroxyl groups are sulfonium-(poly)alkylene glycols (e.g., sulfonium-(poly)alkylene glycol methacrylates) and their salts, or (poly)alkylene glycol dimethacrylates such as 1,4-butanediol dimethacrylate;

The polyalkylene glycol methacrylates may carry one methacrylate group (e.g., polyethylene glycol monomethacrylate, polypropylene glycol monomethacrylate, polybutylene glycol monomethacrylate, polypentylene glycol monomethacrylate or polyhexylene glycol monomethacrylate) or two or more, preferably two, methacrylate groups, such as polyethylene glycol dimethacrylate, polypropylene glycol dimethacrylate, polybutylene glycol dimethacrylate, polypentylene glycol dimethacrylate or polyhexylene glycol dimethacrylate;

The polyalkylene glycol methacrylates may also comprise two or more polyalkylene glycol blocks that are different from one another, examples being blocks of polymethylene glycol and polyethylene glycol, or blocks of polyethylene glycol and polypropylene glycol (e.g., Bisomer PEM63PHD (Cognis), CAS 58916-75-9);

The degree of polymerization of the polyalkylene glycol units or polyalkylene glycol blocks is generally in the range from 1 to 20, preferably in the range from 3 to 10, more preferably in the range from 3 to 6.

Examples of preferred (meth)acrylate comonomers are listed below:

a) 4-hydroxybutyl acrylate b) 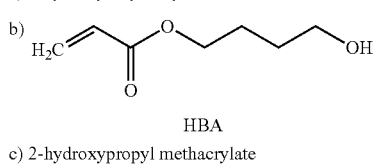

HBA c) 2-hydroxypropyl methacrylate

-continued d) HPMA e) SEM f) PPM 5 Li g) AS h) PEM 6 LD i) PPA 6 j) PEA 6 k) HEMA ammonium sulfatoethyl methacrylate pentapropylene glycol methacrylate acrylic acid hexaethylene glycol methacrylate hexapropylene glycol acrylate hexaethylene glycol acrylate hydroxyethyl methacrylate polyalkylene glycol methacrylate
(CAS No. 589-75-9)

-continued l) Bisomer PEM63PHD m) MPEG 350MA n) 1,3-butanediol dimethacrylate (BDDMA)

o) triethylene glycol dimethacrylate (TEGDMA)

p) hydroxyethyl acrylate (HEA)

q) 2-hydroxypropyl acrylate (HPA)

r) ethylene glycol dimethacrylate (EGDMA)

s) glycidyl methacrylate (GMA)

t) allyl methacrylate (ALMA)

methoxy-polyethylene glycol methacrylate 2-propylheptyl acrylate (2-PHA)

-continued u)
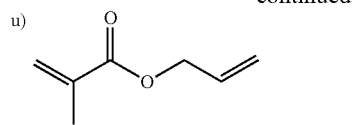
Bisomer PEM 3
(polyethylene glycol methacrylate)

v)
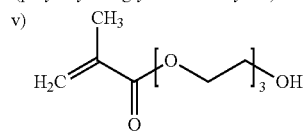
Bisomer IDMA
(isodecyl methacrylate)

w)
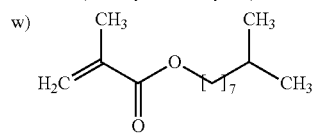
Bisomer C13MA
(isotridecyl methacrylate)

x)
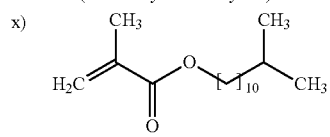
3-sulfopropyl acrylate, more particularly
in salt form such as the potassium salt y)
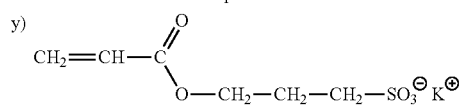
N-(2-acryloyloxyethyl)-N,N-dimethyl-N-(3-
sulfopropyl)ammonium betaine z)
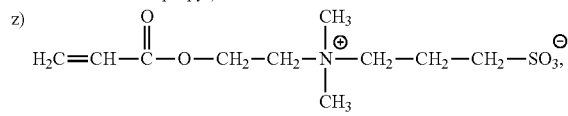
N-(2-methacryloyloxyethyl)-N,N-dimethyl-N-(3-
sulfopropyl)ammonium betaine aa)
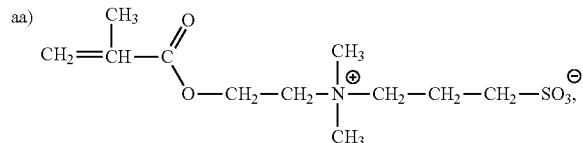
3-sulfopropyl methacrylate, more particularly
in salt form such as the potassium salt bb)
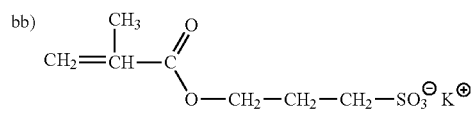
z1) N-(3-methacrylamidopropyl)-N,N-dimethyl-N-(3-
sulfopropyl)ammonium betaine cc)
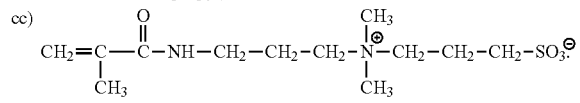

Preferred copolymers c) are bipolymers containing AMPS and one of the aforementioned comonomers a) to z1). Also preferred are bipolymers containing AMPP and one of the aforementioned comonomers a) to z1).

Use may also be made of terpolymers of AMPS or AMPP with two (meth)acrylate monomers.

Where the copolymers c) comprise further monomers as well as AMPS and/or AMPP and (meth)acrylates, these further monomers are preferably selected from the group of the vinyl compounds such as vinyl esters, styrenes, N-vinylcaprolactam, vinylphosphoric acid and its salts and esters, vinylphosphonic acid and its salts and esters, vinylsulfonic acid and its salts and esters, vinylcarboxylic acids and their salts and esters (e.g., vinylacetic acid), unsaturated dicarboxylic or polycarboxylic acids such as maleic esters, or salts of amyl compounds or allyl compounds. Given below are preferred further comonomers for AMPS, AMPP, and (meth)acrylate monomers:

1) Vinyl compounds, e.g., vinyl esters such as vinyl acetate, vinyl laurate, vinyl propionate or vinyl esters of neononanoic acid, N-vinylcaprolactam, vinylphosphoric acid and its salts and esters, vinylphosphonic acid and its salts and esters, vinylsulfonic acid and its salts and esters, vinylcarboxylic acids and their salts and esters (e.g., vinylacetic acid), or aromatic vinyl compounds such as styrene comonomers, for example styrene, alpha-methylstyrene or styrenes with polar functionalization such as styrenes having hydroxyl, amino, nitrile, carboxylic acid, phosphonic acid, phosphoric acid, nitro or sulfonic acid groups, and salts thereof, the polar functionalization of the styrenes being preferably in para position.

2) Unsaturated dicarboxylic or polycarboxylic acids, e.g., maleic esters such as dibutyl maleate or dioctyl maleate, as salts of allyl compounds, e.g., sodium allylsulfonate, and as salts of amyl derivatives, e.g., sodium amylsulfonate.

Preferred copolymers c) therefore include terpolymers containing AMPS, one of the aforementioned comonomers a) to z1), and a further comonomer selected from the group of vinyl compounds such as vinyl esters, styrenes, N-vinylcaprolactam, vinylphosphoric acid and its salts and esters, vinylphosphonic acid and its salts and esters, vinylsulfonic acid and its salts and esters, vinylcarboxylic acids and their salts and esters (e.g., vinylacetic acid), unsaturated dicarboxylic or polycarboxylic acids such as maleic esters, or salts of amyl compounds or allyl compounds.

Preference is also given to terpolymers containing AMPP, one of the aforementioned copolymers a) to z1), and a further comonomers selected from the group of vinyl compounds such as vinyl esters, styrenes, N-vinylcaprolactam, vinylphosphoric acid and its salts and esters, vinylphosphonic acid and its salts and esters, vinylsulfonic acid and its salts and esters, vinylcarboxylic acids and their salts and esters (e.g., vinylacetic acid), unsaturated dicarboxylic or polycarboxylic acids such as maleic esters, or salts of amyl compounds or allyl compounds.

Examples of particularly preferred terpolymers are terpolymers of the type AMPS+HEMA (comonomer i)+vinyl acetate or terpolymers of the type AMPP+HEMA+vinyl acetate, AMPS+HEMA+vinyl propionate, AMPP+HEMA+vinyl propionate, AMPS+HEMA+N-vinylcaprolactam, AMPP+HEMA+N-vinylcaprolactam, AMPS+HEMA+styrene, AMPP+HEMA+styrene, AMPS+HEMA+p-hydroxystyrene, AMPP+HEMA+p-hydroxystyrene, AMPS+HEMA+vinyl laurate, AMPP+HEMA+vinyl laurate, AMPS+HEMA+vinylphosphoric acid, AMPP+HEMA+vinylphosphoric acid, AMPS+HEMA+trimethyl vinylphosphate, AMPP+HEMA+trimethyl vinylphosphate, AMPS+HEMA+vinylphosphonic acid, AMPP+HEMA+vinylphosphonic acid, AMPS+HEMA+dimethyl vinylphosphonate, AMPP+HEMA+dimethyl vinylphosphonate, AMPS+HEMA+vinylsulfonic acid, AMPP+HEMA+vinyisulfonic acid, AMPS+HEMA+vinylacetic acid, AMPP+HEMA+vinylacetic acid;

AMPS+HEA (comonomer o)+vinyl acetate, AMPP+ HEA+vinyl acetate, AMPS+HEA+vinyl propionate, AMPP+ HEA+vinyl propionate, AMPS+HEA+N-vinylcaprolactam, AMPP+HEA+N-vinylcaprolactam, AMPS+HEA+styrene, AMPP+HEA+styrene, AMPS+HEA+p-hydroxystyrene, AMPP+HEA+p-hydroxystyrene, AMPS+HEA+vinyl laurate, AMPP+HEA+vinyl laurate, AMPS+HEA+vinylphosphoric acid, AMPP+HEA+vinylphosphoric acid, AMPS+ HEA+trimethyl vinylphosphate, AMPP+HEA+trimethyl vinylphosphate, AMPS+HEA+vinylphosphonic acid, AMPP+HEA+vinylphosphonic acid, AMPS+HEA+dimethyl vinylphosphonate, AMPP+HEA+dimethyl vinylphosphonate, AMPS+HEA+vinylsulfonic acid, AMPP+HEA+vinylsulfonic acid, AMPS+HEA+vinylacetic acid, AMPP+ HEA+vinylacetic acid;

AMPS+HPMA (comonomer b)+vinyl acetate, AMPP+ HPMA+vinyl acetate, AMPS+HPMA+vinyl propionate, AMPP+HPMA+vinyl propionate, AMPS+HPMA+N-vinylcaprolactam, AMPP+HPMA+N-vinylcaprolactam, AMPS+ HPMA+styrene, AMPP+HPMA+styrene, AMPS+HPMA+ p-hydroxystyrene, AMPP+HPMA+p-hydroxystyrene, AMPS+HPMA+vinyl laurate, AMPP+HPMA+vinyl laurate, AMPS+HPMA+vinylphosphoric acid, AMPP+HPMA+vinylphosphoric acid, AMPS+HPMA+trimethyl vinylphosphate, AMPP+HPMA+trimethyl vinylphosphate, AMPS+ HPMA+vinylphosphonic acid, AMPP+HPMA+ vinylphosphonic acid, AMPS+HPMA+dimethyl vinylphosphonate, AMPP+HPMA+dimethyl vinylphosphonate, AMPS+HPMA+vinylsulfonic acid, AMPP+HPMA+vinylsulfonic acid, AMPS+HPMA+vinylacetic acid, AMPP+ HPMA+vinylacetic acid;

AMPS+HPA (comonomer p)+vinyl acetate, AMPP+ HPA+vinyl acetate, AMPS+HPA+vinyl propionate, AMPP+ HPA+vinyl propionate, AMPS+HPA+N-vinylcaprolactam, AMPP+HPA+N-vinylcaprolactam, AMPS+HPA+styrene, AMPP+HPA+styrene, AMPS+HPA+p-hydroxystyrene, AMPP+HPA+p-hydroxystyrene, AMPS+HPA+vinyl laurate, AMPP+HPA+vinyl laurate, AMPS+HPA+vinylphosphoric acid, AMPP+HPA+vinylphosphoric acid, AMPS+ HPA+trimethyl vinylphosphate, AMPP+HPA+trimethyl vinylphosphate, AMPS+HPA+vinylphosphonic acid, AMPP+HPA+vinylphosphonic acid, AMPS+HPA+dimethyl vinylphosphonate, AMPP+HPA+dimethyl vinyiphosphonate, AMPS+HPA+vinylsulfonic acid, AMPP+HPA+vinylsulfonic acid, AMPS+HPA+vinylacetic acid, AMPP+HPA+ vinylacetic acid;

AMPS+HBA (comonomer a)+vinyl acetate, AMPP+ HBA+vinyl acetate, AMPS+HBA+vinyl propionate, AMPP+ HBA+vinyl propionate, AMPS+HBA+N-vinylcaprolactam, AMPP+HBA+N-vinylcaprolactam, AMPS+HBA+styrene, AMPP+HBA+styrene, AMPS+HBA+p-hydroxystyrene, AMPP+HBA+p-hydroxystyrene, AMPS+HBA+vinyl laurate, AMPP+HBA+vinyl laurate, AMPS+HBA+vinylphosphoric acid, AMPP+HBA+vinylphosphoric acid, AMPS+ HBA+trimethyl vinylphosphate, AMPP+HBA+trimethyl vinylphosphate, AMPS+HBA+vinylphosphonic acid, AMPP+HBA+vinylphosphonic acid, AMPS+HBA+dimethyl vinylphosphonate, AMPP+HBA+dimethyl vinyiphosphonate, AMPS+HBA+vinylsulfonic acid, AMPS+HBA+vinylsulfonic acid, AMPS+HBA+vinylacetic acid, AMPP+ HBA+vinylacetic acid;

AMPS+PEM6LD (comonomer f)+vinyl acetate, AMPP+ PEM6LD+vinyl acetate, AMPS+PEM6LD+vinyl propionate, AMPP+PEM6LD+vinyl propionate, AMPS+ PEM6LD+N-vinylcaprolactam, AMPP+PEM6LD+N-vinylcaprolactam, AMPS+PEM6LD+styrene, AMPP+ PEM6LD+styrene, AMPS+PEM6LD+p-hydroxystyrene, AMPP+PEM6LD+p-hydroxystyrene, AMPS+PEM6LD+vinyl laurate, AMPP+PEM6LD+vinyl laurate, AMPS+ PEM6LD+vinylphosphoric acid, AMPP+PEM6LD+vinylphosphoric acid, AMPS+PEM6LD+trimethyl vinylphosphate, AMPP+PEM6LD+trimethyl vinylphosphate, AMPS+PEM6LD+vinylphosphonic acid, AMPP+ PEM6LD+vinylphosphonic acid, AMPS+PEM6LD+dimethyl vinylphosphonate, AMPP+PEM6LD+dimethyl vinylphosphonate, AMPS+PEM6LD+vinylsulfonic acid, AMPP+PEM6LD+vinylsulfonic acid, AMPS+PEM6LD+vinylacetic acid, AMPP+PEM6LD+vinylacetic acid;

AMPS+PPA6 (comonomer g)+vinyl acetate, AMPP+ PPA6+vinyl acetate, AMPS+PPA6+vinyl propionate, AMPP+PPA6+vinyl propionate, AMPS+PPA6+N-vinylcaprolactam, AMPP+PPA6+N-vinylcaprolactam, AMPS+ PPA6+styrene, AMPP+PPA6+styrene, AMPS+PPA6+p-hydroxystyrene, AMPP+PPA6+p-hydroxystyrene, AMPS+ PPA6+vinyl laurate, AMPP+PPA6+vinyl laurate, AMPS+ PPA6+vinylphosphoric acid, AMPP+PPA6+vinylphosphoric acid, AMPS+PPA6+trimethyl vinylphosphate, AMPP+ PPA6+trimethyl vinylphosphate, AMPS+PPA6+vinylphosphonic acid, AMPP+PPA6+vinylphosphonic acid, AMPS+ PPA6+dimethyl vinylphosphonate, AMPP+PPA6+dimethyl vinylphosphonate, AMPS+PPA6+vinylsulfonic acid, AMPP+PPA6+vinylsulfonic acid, AMPS+PPA6+vinylacetic acid, AMPP+PPA6+vinylacetic acid;

Also possible are tetrapolymers, e.g., AMPS or AMPP+ HEMA+vinyl acetate, and higher copolymers through incorporation of further comonomers, depending on profile of properties and profile of requirements.

The copolymers c) generally have a fraction of AMPS units or AMPP units of greater than 50 mol %, preferably in the range of 60-95 mol %, more preferably of 80-99 mol %; the fraction of the further monomers is generally less than 50 mol %, preferably in the range from 5 to 40 mol %, more preferably from 0.1 to 20 mol %. The fraction of (meth)acrylate monomers in bipolymers is generally in the range from 0.1 mol % to 40 mol %, while in terpolymers it is in the range from 0.1 mol % to 20 mol %. The fraction of further monomers in terpolymers is generally in the range from 0.1 mol % to 5 mol %.

The copolymers c) may be obtained by conventional methods, as for example by a batch or semibatch process. For example, first of all, corresponding amounts of water and monomers are conveyed into a thermostattable reactor, and are placed under an inert gas atmosphere. This initial charge is then stirred and brought to reaction temperature (preferably in the region of around 70-80° C.), and initiator is added, preferably in the form of an aqueous solution. Suitable initiators are known initiators for radical polymerizations, examples being sodium, potassium or ammonium peroxodisulfate, or $H_2O_2$ based mixtures, examples being mixtures of $H_2O_2$ with citric acid. The maximum temperature is awaited and, as soon as the temperature in the reactor falls, either a) the remaining monomers are metered in, followed by an after-reaction (semibatch process), or b) the after-reaction takes place directly (batch process). After that, the resulting reaction mixture is cooled to room temperature and the copolymer is isolated from the aqueous solution, as for example by extraction with organic solvents such as hexane or methylene chloride, with subsequent distillative removal of the solvent. Thereafter the copolymer may be washed with organic solvent and dried. The reaction mixture obtained may also be subjected directly to further processing, in which case it is an advantage to add a preservative to the aqueous copolymer solution.

The copolymers are suitable as protective colloids in the production of microcapsules. Preferred microcapsules of the present invention have the following components a), b), and c):

phloroglucinol, glutaraldehyde, AMPS/hydroxyethyl methacrylate copolymer;
phloroglucinol, succinaldehyde, AMPS/hydroxyethyl methacrylate copolymer;
phloroglucinol, glyoxal, AMPS/hydroxyethyl methacrylate copolymer;
phloroglucinol, glyoxylic acid, AMPS/hydroxyethyl methacrylate copolymer;
phloroglucinol, glutaraldehyde, AMPS/hydroxyethyl acrylate copolymer;
phloroglucinol, succinaldehyde, AMPS/hydroxyethyl acrylate copolymer;
phloroglucinol, glyoxal, AMPS/hydroxyethyl acrylate copolymer;
phloroglucinol, glyoxylic acid, AMPS/hydroxyethyl acrylate copolymer;
phloroglucinol, glutaraldehyde, AMPS/hydroxypropyl methacrylate copolymer;
phloroglucinol, succinaldehyde, AMPS/hydroxypropyl methacrylate copolymer;
phloroglucinol, glyoxal, AMPS/hydroxypropyl methacrylate copolymer;
phloroglucinol, glyoxylic acid, AMPS/hydroxypropyl methacrylate copolymer;
phloroglucinol, glutaraldehyde, AMPS/hydroxypropyl acrylate copolymer;
phloroglucinol, succinaldehyde, AMPS/hydroxypropyl acrylate copolymer;
phloroglucinol, glyoxal, AMPS/hydroxypropyi acrylate copolymer;
phloroglucinol, glyoxylic acid, AMPS/hydroxypropyl acrylate copolymer;
phloroglucinol, glutaraldehyde, AMPS/hydroxybutyl methacrylate copolymer;
phloroglucinol, succinaldehyde, AMPS/hydroxybutyl methacrylate copolymer;
phloroglucinol, glyoxal, AMPS/hydroxybutyl methacrylate copolymer;
phloroglucinol, glyoxylic acid, AMPS/hydroxybutyl methacrylate copolymer;
phloroglucinol, glutaraldehyde, AMPS/hydroxybutyl acrylate copolymer;
phloroglucinol, succinaldehyde, AMPS/hydroxybutyl acrylate copolymer;
phloroglucinol, glyoxal, AMPS/hydroxybutyl acrylate copolymer;
phloroglucinol, glyoxylic acid, AMPS/hydroxybutyl acrylate copolymer;
phloroglucinol, glutaraldehyde, AMPS/polyethylene glycol monomethacrylate copolymer;
phloroglucinol, succinaldehyde, AMPS/polyethylene glycol monomethacrylate copolymer;
phloroglucinol, glyoxal, AMPS/polyethylene glycol monomethacrylate copolymer;
phloroglucinol, glyoxylic acid, AMPS/polyethylene glycol monomethacrylate copolymer;
phloroglucinol, glutaraldehyde, AMPS/polyethylene glycol monoacrylate copolymer;
phloroglucinol, succinaldehyde, AMPS/polyethylene glycol monoacrylate copolymer;
phloroglucinol, glyoxal, AMPS/polyethylene glycol monoacrylate copolymer;
phloroglucinol, glyoxylic acid, AMPS/polyethylene glycol monoacrylate copolymer;
phloroglucinol, glutaraldehyde, AMPS/polypropylene glycol monomethacrylate copolymer;
phloroglucinol, succinaldehyde, AMPS/polypropylene glycol monomethacrylate copolymer;
phloroglucinol, glyoxal, AMPS/polypropylene glycol monomethacrylate copolymer;
phloroglucinol, glyoxylic acid, AMPS/polypropylene glycol monomethacrylate copolymer;
phloroglucinol, glutaraldehyde, AMPS/polypropylene glycol monoacrylate copolymer;
phloroglucinol, succinaldehyde, AMPS/polypropylene glycol monoacrylate copolymer;
phloroglucinol, glyoxal, AMPS/polypropylene glycol monoacrylate copolymer;
phloroglucinol, glyoxylic acid, AMPS/polypropylene glycol monoacrylate copolymer;
phloroglucinol, glutaraldehyde, AMPS/methoxy-polyethylene glycol monomethacrylate copolymer;
phloroglucinol, succinaldehyde, AMPS/methoxy-polyethylene glycol monomethacrylate copolymer;
phloroglucinol, glyoxal, AMPS/methoxy-polyethylene glycol monomethacrylate copolymer;
phloroglucinol, glyoxylic acid, AMPS/methoxy-polyethylene glycol monomethacrylate copolymer;
phloroglucinol, glutaraldehyde, AMPS/methoxy-polyethylene glycol monoacrylate copolymer;
phloroglucinol, succinaldehyde, AMPS/methoxy-polyethylene glycol monoacrylate copolymer;
phloroglucinol, glyoxal, AMPS/methoxy-polyethylene glycol monoacrylate copolymer;
phloroglucinol, glyoxylic acid, AMPS/methoxy-polyethylene glycol monoacrylate copolymer;
resorcinol, glutaraldehyde, AMPS/hydroxyethyl methacrylate copolymer;
resorcinol, succinaldehyde, AMPS/hydroxyethyl methacrylate copolymer;
resorcinol, glyoxal, AMPS/hydroxyethyl methacrylate copolymer;
resorcinol, glyoxylic acid, AMPS/hydroxyethyl methacrylate copolymer;
resorcinol, glutaraldehyde, AMPS/hydroxyethyl acrylate copolymer;
resorcinol, succinaldehyde, AMPS/hydroxyethyl acrylate copolymer;
resorcinol, glyoxal, AMPS/hydroxyethyl acrylate copolymer;
resorcinol, glyoxylic acid, AMPS/hydroxyethyl acrylate copolymer;
resorcinol, glutaraldehyde, AMPS/hydroxypropyl methacrylate copolymer;
resorcinol, succinaldehyde, AMPS/hydroxypropyl methacrylate copolymer;
resorcinol, glyoxal, AMPS/hydroxypropyl methacrylate copolymer;
resorcinol, glyoxylic acid, AMPS/hydroxypropyl methacrylate copolymer;
resorcinol, glutaraldehyde, AMPS/hydroxypropyl acrylate copolymer;
resorcinol, succinaldehyde, AMPS/hydroxypropyl acrylate copolymer;
resorcinol, glyoxal, AMPS/hydroxypropyl acrylate copolymer;
resorcinol, glyoxylic acid, AMPS/hydroxypropyl acrylate copolymer;

resorcinol, glutaraldehyde, AMPS/hydroxybutyl methacrylate copolymer;
resorcinol, succinaldehyde, AMPS/hydroxybutyl methacrylate copolymer;
resorcinol, glyoxal, AMPS/hydroxybutyl methacrylate copolymer;
resorcinol, glyoxylic acid, AMPS/hydroxybutyl methacrylate copolymer;
resorcinol, glutaraldehyde, AMPS/hydroxybutyl acrylate copolymer;
resorcinol, succinaldehyde, AMPS/hydroxybutyl acrylate copolymer;
resorcinol, glyoxal, AMPS/hydroxybutyl acrylate copolymer;
resorcinol, glyoxylic acid, AMPS/hydroxybutyl acrylate copolymer;
resorcinol, glutaraldehyde, AMPS/polyethylene glycol monomethacrylate copolymer;
resorcinol, succinaldehyde, AMPS/polyethylene glycol monomethacrylate copolymer;
resorcinol, glyoxal, AMPS/polyethylene glycol monomethacrylate copolymer;
resorcinol, glyoxylic acid, AMPS/polyethylene glycol monomethacrylate copolymer;
resorcinol, glutaraldehyde, AMPS/polyethylene glycol monoacrylate copolymer;
resorcinol, succinaldehyde, AMPS/polyethylene glycol monoacrylate copolymer;
resorcinol, glyoxal, AMPS/polyethylene glycol monoacrylate copolymer;
resorcinol, glyoxylic acid, AMPS/polyethylene glycol monoacrylate copolymer;
resorcinol, glutaraldehyde, AMPS/polypropylene glycol monomethacrylate copolymer;
resorcinol, succinaldehyde, AMPS/polypropylene glycol monomethacrylate copolymer;
resorcinol, glyoxal, AMPS/polypropylene glycol monomethacrylate copolymer;
resorcinol, glyoxylic acid, AMPS/polypropylene glycol monomethacrylate copolymer;
resorcinol, glutaraldehyde, AMPS/polypropylene glycol monoacrylate copolymer;
resorcinol, succinaldehyde, AMPS/polypropylene glycol monoacrylate copolymer;
resorcinol, glyoxal, AMPS/polypropylene glycol monoacrylate copolymer;
resorcinol, glyoxylic acid, AMPS/polypropylene glycol monoacrylate copolymer;
resorcinol, glutaraldehyde, AMPS/methoxy-polyethylene glycol monomethacrylate copolymer;
resorcinol, succinaldehyde, AMPS/methoxy-polyethylene glycol monomethacrylate copolymer;
resorcinol, glyoxal, AMPS/methoxy-polyethylene glycol monomethacrylate copolymer;
resorcinol, glyoxylic acid, AMPS/methoxy-polyethylene glycol monomethacrylate copolymer;
resorcinol, glutaraldehyde, AMPS/methoxy-polyethylene glycol monoacrylate copolymer;
resorcinol, succinaldehyde, AMPS/methoxy-polyethylene glycol monoacrylate copolymer;
resorcinol, glyoxal, AMPS/methoxy-polyethylene glycol monoacrylate copolymer;
resorcinol, glyoxylic acid, AMPS/methoxy-polyethylene glycol monoacrylate copolymer;
urea, glutaraldehyde, AMPS/hydroxyethyl methacrylate copolymer;
urea, succinaldehyde, AMPS/hydroxyethyl methacrylate copolymer;
urea, glyoxal, AMPS/hydroxyethyl methacrylate copolymer;
urea, glyoxylic acid, AMPS/hydroxyethyl methacrylate copolymer;
urea, glutaraldehyde, AMPS/hydroxyethyl acrylate copolymer;
urea, succinaldehyde, AMPS/hydroxyethyl acrylate copolymer;
urea, glyoxal, AMPS/hydroxyethyl acrylate copolymer;
urea, glyoxylic acid, AMPS/hydroxyethyl acrylate copolymer;
urea, glutaraldehyde, AMPS/hydroxypropyl methacrylate copolymer;
urea, succinaldehyde, AMPS/hydroxypropyl methacrylate copolymer;
urea, glyoxal, AMPS/hydroxypropyl methacrylate copolymer;
urea, glyoxylic acid, AMPS/hydroxypropyl methacrylate copolymer;
urea, glutaraldehyde, AMPS/hydroxypropyl acrylate copolymer;
urea, succinaldehyde, AMPS/hydroxypropyl acrylate copolymer;
urea, glyoxal, AMPS/hydroxypropyl acrylate copolymer;
urea, glyoxylic acid, AMPS/hydroxypropyl acrylate copolymer;
urea, glutaraldehyde, AMPS/hydroxybutyl methacrylate copolymer;
urea, succinaldehyde, AMPS/hydroxybutyl methacrylate copolymer;
urea, glyoxal, AMPS/hydroxybutyl methacrylate copolymer;
urea, glyoxylic acid, AMPS/hydroxybutyl methacrylate copolymer;
urea, glutaraldehyde, AMPS/hydroxybutyl acrylate copolymer;
urea, succinaldehyde, AMPS/hydroxybutyl acrylate copolymer;
urea, glyoxal, AMPS/hydroxybutyl acrylate copolymer;
urea, glyoxylic acid, AMPS/hydroxybutyl acrylate copolymer;
urea, glutaraldehyde, AMPS/polyethylene glycol monomethacrylate copolymer;
urea, succinaldehyde, AMPS/polyethylene glycol monomethacrylate copolymer;
urea, glyoxal, AMPS/polyethylene glycol monomethacrylate copolymer;
urea, glyoxylic acid, AMPS/polyethylene glycol monomethacrylate copolymer;
urea, glutaraldehyde, AMPS/polyethylene glycol monoacrylate copolymer;
urea, succinaldehyde, AMPS/polyethylene glycol monoacrylate copolymer;
urea, glyoxal, AMPS/polyethylene glycol monoacrylate copolymer;
urea, glyoxylic acid, AMPS/polyethylene glycol monoacrylate copolymer;
urea, glutaraldehyde, AMPS/polypropylene glycol monomethacrylate copolymer;
urea, succinaldehyde, AMPS/polypropylene glycol monomethacrylate copolymer;
urea, glyoxal, AMPS/polypropylene glycol monomethacrylate copolymer;
urea, glyoxylic acid, AMPS/polypropylene glycol monomethacrylate copolymer;
urea, glutaraldehyde, AMPS/polypropylene glycol monoacrylate copolymer;

urea, succinaldehyde, AMPS/polypropylene glycol monoacrylate copolymer;
urea, glyoxal, AMPS/polypropylene glycol monoacrylate copolymer;
urea, glyoxylic acid, AMPS/polypropylene glycol monoacrylate copolymer;
urea, glutaraldehyde, AMPS/methoxy-polyethylene glycol monomethacrylate copolymer;
urea, succinaldehyde, AMPS/methoxy-polyethylene glycol monomethacrylate copolymer;
urea, glyoxal, AMPS/methoxy-polyethylene glycol monomethacrylate copolymer;
urea, glyoxylic acid, AMPS/methoxy-polyethylene glycol monomethacrylate copolymer;
urea, glutaraldehyde, AMPS/methoxy-polyethylene glycol monoacrylate copolymer;
urea, succinaldehyde, AMPS/methoxy-polyethylene glycol monoacrylate copolymer;
urea, glyoxal, AMPS/methoxy-polyethylene glycol monoacrylate copolymer;
urea, glyoxylic acid, AMPS/methoxy-polyethylene glycol monoacrylate copolymer;
melamine, glutaraldehyde, AMPS/hydroxyethyl methacrylate copolymer;
melamine, succinaldehyde, AMPS/hydroxyethyl methacrylate copolymer;
melamine, glyoxal, AMPS/hydroxyethyl methacrylate copolymer;
melamine, glyoxylic acid, AMPS/hydroxyethyl methacrylate copolymer;
melamine, glutaraldehyde, AMPS/hydroxyethyl acrylate copolymer;
melamine, succinaldehyde, AMPS/hydroxyethyl acrylate copolymer;
melamine, glyoxal, AMPS/hydroxyethyl acrylate copolymer;
melamine, glyoxylic acid, AMPS/hydroxyethyl acrylate copolymer;
melamine, glutaraldehyde, AMPS/hydroxypropyl methacrylate copolymer;
melamine, succinaldehyde, AMPS/hydroxypropyl methacrylate copolymer;
melamine, glyoxal, AMPS/hydroxypropyl methacrylate copolymer;
melamine, glyoxylic acid, AMPS/hydroxypropyl methacrylate copolymer;
melamine, glutaraldehyde, AMPS/hydroxypropyl acrylate copolymer;
melamine, succinaldehyde, AMPS/hyd roxypropyl acrylate copolymer;
melamine, glyoxal, AMPS/hydroxypropyl acrylate copolymer;
melamine, glyoxylic acid, AMPS/hydroxypropyl acrylate copolymer;
melamine, glutaraldehyde, AMPS/hydroxybutyl methacrylate copolymer;
melamine, succinaldehyde, AMPS/hydroxybutyl methacrylate copolymer;
melamine, glyoxal, AMPS/hydroxybutyl methacrylate copolymer;
melamine, glyoxylic acid, AMPS/hydroxybutyl methacrylate copolymer;
melamine, glutaraldehyde, AMPS/hydroxybutyl acrylate copolymer;
melamine, succinaldehyde, AMPS/hydroxybutyl acrylate copolymer;
melamine, glyoxal, AMPS/hydroxybutyl acrylate copolymer;
melamine, glyoxylic acid, AMPS/hydroxybutyl acrylate copolymer;
melamine, glutaraldehyde, AMPS/polyethylene glycol monomethacrylate copolymer;
melamine, succinaldehyde, AMPS/polyethylene glycol monomethacrylate copolymer;
melamine, glyoxal, AMPS/polyethylene glycol monomethacrylate copolymer;
melamine, glyoxylic acid, AMPS/polyethylene glycol monomethacrylate copolymer;
melamine, glutaraldehyde, AMPS/polyethylene glycol monoacrylate copolymer;
melamine, succinaldehyde, AMPS/polyethylene glycol monoacrylate copolymer;
melamine, glyoxal, AMPS/polyethylene glycol monoacrylate copolymer;
melamine, glyoxylic acid, AMPS/polyethylene glycol monoacrylate copolymer;
melamine, glutaraldehyde, AMPS/polypropylene glycol monomethacrylate copolymer;
melamine, succinaldehyde, AMPS/polypropylene glycol monomethacrylate copolymer;
melamine, glyoxal, AMPS/polypropylene glycol monomethacrylate copolymer;
melamine, glyoxylic acid, AMPS/polypropylene glycol monomethacrylate copolymer;
melamine, glutaraldehyde, AMPS/polypropylene glycol monoacrylate copolymer;
melamine, succinaldehyde, AMPS/polypropylene glycol monoacrylate copolymer;
melamine, glyoxal, AMPS/polypropylene glycol monoacrylate copolymer;
melamine, glyoxylic acid, AMPS/polypropylene glycol monoacrylate copolymer;
melamine, glutaraldehyde, AMPS/methoxy-polyethylene glycol monomethacrylate copolymer;
melamine, succinaldehyde, AMPS/methoxy-polyethylene glycol monomethacrylate copolymer;
melamine, glyoxal, AMPS/methoxy-polyethylene glycol monomethacrylate copolymer;
melamine, glyoxylic acid, AMPS/methoxy-polyethylene glycol monomethacrylate copolymer;
melamine, glutaraldehyde, AMPS/methoxy-polyethylene glycol monoacrylate copolymer;
melamine, succinaldehyde, AMPS/methoxy-polyethylene glycol monoacrylate copolymer;
melamine, glyoxal, AMPS/methoxy-polyethylene glycol monoacrylate copolymer;
melamine, glyoxylic acid, AMPS/methoxy-polyethylene glycol monoacrylate copolymer.

Likewise suitable for the microcapsules of the invention are combinations wherein the aforementioned components a) and b) are present and AMPP instead of AMPS is present as component c). Of these, the following AMPP combinations are particularly preferred:

resorcinol, glutaraldehyde, AMPP/polyethylene glycol monomethacrylate copolymer;
resorcinol, succinaldehyde, AMPP/polyethylene glycol monomethacrylate copolymer;
resorcinol, glyoxal, AMPP/polyethylene glycol monomethacrylate copolymer;
resorcinol, glyoxylic acid, AMPP/polyethylene glycol monomethacrylate copolymer;
resorcinol, glutaraldehyde, AMPP/polyethylene glycol monoacrylate copolymer;

resorcinol, succinaldehyde, AMPP/polyethylene glycol monoacrylate copolymer;
resorcinol, glyoxal, AMPP/polyethylene glycol monoacrylate copolymer;
resorcinol, glyoxylic acid, AMPP/polyethylene glycol monoacrylate copolymer;
resorcinol, glutaraldehyde, AMPP/polypropylene glycol monomethacrylate copolymer;
resorcinol, succinaldehyde, AMPP/polypropylene glycol monomethacrylate copolymer;
resorcinol, glyoxal, AMPP/polypropylene glycol monomethacrylate copolymer;
resorcinol, glyoxylic acid, AMPP/polypropylene glycol monomethacrylate copolymer;
resorcinol, glutaraldehyde, AMPP/polypropylene glycol monoacrylate copolymer;
resorcinol, succinaldehyde, AMPP/polypropylene glycol monoacrylate copolymer;
resorcinol, glyoxal, AMPP/polypropylene glycol monoacrylate copolymer;
resorcinol, glyoxylic acid, AMPP/polypropylene glycol monoacrylate copolymer;
resorcinol, glutaraldehyde, AMPP/methoxy-polyethylene glycol monomethacrylate copolymer;
resorcinol, succinaldehyde, AMPP/methoxy-polyethylene glycol monomethacrylate copolymer;
resorcinol, glyoxal, AMPP/methoxy-polyethylene glycol monomethacrylate copolymer;
resorcinol, glyoxylic acid, AMPP/methoxy-polyethylene glycol monomethacrylate copolymer;
resorcinol, glutaraldehyde, AMPP/methoxy-polyethylene glycol monoacrylate copolymer;
resorcinol, succinaldehyde, AMPP/methoxy-polyethylene glycol monoacrylate copolymer;
resorcinol, glyoxal, AMPP/methoxy-polyethylene glycol monoacrylate copolymer;
resorcinol, glyoxylic acid, AMPS/methoxypolyethylene glycol monoacrylate copolymer;
phloroglucinol, glutaraldehyde, AMPP/polyethylene glycol monomethacrylate copolymer;
phloroglucinol, succinaldehyde, AMPP/polyethylene glycol monomethacrylate copolymer;
phloroglucinol, glyoxal, AMPP/polyethylene glycol monomethacrylate copolymer;
phloroglucinol, glyoxylic acid, AMPS/polyethylene glycol monomethacrylate copolymer;
phloroglucinol, glutaraldehyde, AMPP/polyethylene glycol monoacrylate copolymer;
phloroglucinol, succinaldehyde, AMPP/polyethylene glycol monoacrylate copolymer;
phloroglucinol, glyoxal, AMPP/polyethylene glycol monoacrylate copolymer;
phloroglucinol, glyoxylic acid, AMPP/polyethylene glycol monoacrylate copolymer;
phloroglucinol, glutaraldehyde, AMPP/polypropylene glycol monomethacrylate copolymer;
phloroglucinol, succinaldehyde, AMPP/polypropylene glycol monomethacrylate copolymer;
phloroglucinol, glyoxal, AMPP/polypropylene glycol monomethacrylate copolymer;
phloroglucinol, glyoxylic acid, AMPP/polypropylene glycol monomethacrylate copolymer;
phloroglucinol, glutaraldehyde, AMPP/polypropylene glycol monoacrylate copolymer;
phloroglucinol, succinaldehyde, AMPP/polypropylene glycol monoacrylate copolymer;
phloroglucinol, glyoxal, AMPP/polypropylene glycol monoacrylate copolymer;
phloroglucinol, glyoxylic acid, AMPP/polypropylene glycol monoacrylate copolymer;
phloroglucinol, glutaraldehyde, AMPP/methoxy-polyethylene glycol monomethacrylate copolymer;
phloroglucinol, succinaldehyde, AMPP/methoxy-polyethylene glycol monomethacrylate copolymer;
phloroglucinol, glyoxal, AMPP/methoxy-polyethylene glycol monomethacrylate copolymer;
phloroglucinol, glyoxylic acid, AMPP/methoxy-polyethylene glycol monomethacrylate copolymer;
phloroglucinol, glutaraldehyde, AMPP/methoxy-polyethylene glycol monoacrylate copolymer;
phloroglucinol, succinaldehyde, AMPP/methoxy-polyethylene glycol monoacrylate copolymer;
phloroglucinol, glyoxal, AMPP/methoxy-polyethylene glycol monoacrylate copolymer;
phloroglucinol, glyoxylic acid, AMPP/methoxypolyethylene glycol monoacrylate copolymer.

Also suitable for the microcapsules of the invention are combinations with two or more components a), more particularly the abovementioned combinations in which component a) is replaced by a combination of two or more compounds a), preferably by two amines a1) or by two aromatic or heteroaromatic compounds a2). Also suitable are the aforementioned combinations in which component a) consists of a combination of components a1) and a2). Examples of such combinations with more than one component a) are given below:

phloroglucinol/melamine, glutaraldehyde, AMPS/methoxypolyethylene glycol monoacrylate copolymer;
resorcinol/melamine, glutaraldehyde, AMPS/methoxy-polyethylene glycol monoacrylate copolymer;
urea/melamine, glutaraldehyde, AMPS/methoxy-polyethylene glycol monoacrylate copolymer;
urea/melamine, glutaraldehyde, AMPP/methoxy-polyethylene glycol monoacrylate copolymer.

The invention also encompasses physical mixtures of different microcapsules, so that, consequently, capsule mixtures based on the aforementioned microcapsule systems in every possible combination are encompassed. The properties in this case may be adjusted in accordance with requirements, through the nature of the mixed microcapsules and their mixing ratio.

An example of one such mixture of microcapsules is a combination of microcapsules of melamine, glutaraldehyde, AMPS, and PEM63PHD with microcapsules of phloroglucinol, glutaraldehyde, AMPS, and PEM63PHD, in proportions, for example, of 5:95 to 95:5, it being possible for the properties to be adjusted in accordance with requirements—in the case of fragrance oil as core material, a higher storage stability or a fragrance release (boost) with long-term stability.

In one embodiment of the invention it is additionally possible to use one or more agents containing silicon dioxide, such as amorphous hydrophobic silica gel, for producing the microcapsules of the invention. These agents are suitable more particularly for the aftertreatment of the surface of the microcapsules, for the purpose, for example, of reducing the agglomeration tendency.

In one embodiment of the invention, the microcapsules of the invention can also be aftertreated using one or more nitrogen-containing or oxygen-containing agents. Examples of suitable oxygen-containing agents are, more particularly, resorcinol and phloroglucinol.

Among the nitrogen-containing agents it is preferred to employ heterocyclic compounds having at least one nitrogen atom as heteroatom, adjacent either to an amino-substituted carbon atom or to a carbonyl group, such as, for example, pyridazine, pyrimidine, pyrazine, pyrrolidone, aminopyridine, and compounds derived therefrom. Advantageous compounds of this generic kind are aminotriazines and compounds derived therefrom. Suitable aminotriazines are in principle all aminotriazines, such as, for example, melamine, 2,6-diaminotriazine, substituted and dimeric aminotriazines, and mixtures prepared from these compounds. Also advantageous are polyamides and dicyandiamide, urea and its derivatives, and pyrrolidone and compounds derived therefrom. Examples of suitable pyrrolidones are, for example, imidazolidinone and compounds derived therefrom, such as hydantoin, for example, whose derivatives are particularly advantageous; particularly advantageous among these compounds are allantoin and its derivatives. Also particularly advantageous are triamino-1,3,5-triazine (melamine) and its derivatives.

It should be emphasized particularly that the aftertreatment represents a "pure" aftertreatment of the surface, in order to arrive at this preferred embodiment of the microcapsules of the invention. In other words, in this preferred embodiment, the nitrogen-containing, oxygen-containing or silicon-containing agent used is not uniformly involved in the construction of the entire capsule wall, but is instead concentrated predominantly on to the outer surface of the capsule walls. The compounds used for aftertreatment are employed preferably in the form of slurries.

The present invention additionally provides microcapsule dispersions which comprise one or more of the microcapsules of the invention.

The present invention further provides for the use of at least one amine a1) for reaction in accordance with the invention, and/or of at least one aromatic or heteroaromatic compound such as an aromatic alcohol (or derivative thereof, more particularly ether thereof) a2), for reaction with an aldehydic component b) for reaction in accordance with the invention, to form the capsule walls of microcapsules. The free alcohol or ether thereof here may also be present in the form of a mixture. It is preferred for use in accordance with the invention to provide formaldehyde-free microcapsules. However, small amounts of formaldehyde may be added to the reaction mixture, generally less than 0.05% by weight, preferably less than 0.01% by weight, in each case based on the overall mixture, as a preservative, for example.

The present invention is based, as further subject matter, on a method for producing the microcapsules or microcapsule dispersions of the invention, in which at least one amine and/or aromatic or heteroaromatic compound such as an aromatic alcohol, at least one aldehydic component which has at least two C atoms per molecule, and in the presence of at least one copolymer which comprises units of AMPS and/or AMPP and one or more (meth)acrylate monomers, optionally in the presence of at least one substance to be encapsulated (core material), are combined and reacted, and the curing of the capsules takes place by later temperature increase. In this case it is particularly preferred for the pH to be raised in the course of the method, more particularly prior to curing.

Preferably, in the method of the invention, first of all at least one amine a1) and/or at least one aromatic or heteroaromatic compound such as an aromatic alcohol and/or derivative thereof (e.g., ester) or ether thereof a2), and at least one aldehydic component b), in the presence of at least one copolymer c) which contains units of AMPS and/or AMPP and one or more (meth)acrylate monomers, and at least one substance for encapsulation, are combined at a temperature of 40 to 65° C. and at a pH of between 6 and 9, preferably between 7 and 8.5, and in a later method step, at a temperature of 40 to 65° C., the pH is adjusted to between 2 and 11, preferably, in the case of resorcinol, to more than 9, preferably between 9.5 and 11, in the case of phloroglucinol to less than 4, preferably between 3 and 4, and in the case of melamine and urea in the range from 2 to 7, preferably between 3 and 6, and later the curing of the capsules is carried out by temperature increase to 40° C. to 110° C., preferably 70° C. to 90° C., more particularly 80° C.

Through the selected parameters of metering rate, temperature, pH and/or stirring speed it is possible to influence the yield and quality of the microcapsules or microcapsule dispersions of the invention. More particularly, too low a temperature may result in the capsule wall being less impervious. This is evident to the skilled person from a persistent oil phase, reduced yield, and deposition of core material as a condensate in the filter of the dryer. On the other hand, care ought to be taken to ensure that the reaction rate is not too high, since otherwise only a small amount of wall material surrounds the capsules, and/or excessive free wall material is present outside the capsules. This free wall material may then be present in particles which are larger than the capsules.

The alkalinity may likewise be important for the quality of microcapsules of the invention. In addition, the pH influences the tendency for the batch to gel, in the context of the procedural regime.

In one embodiment of the method of the invention the alkalinity is adjusted using an alkali metal salt, preferably alkali metal carbonate, more particularly sodium carbonate. Sodium carbonate is preferred, since it reduces the risk of gelling. For particular profiles of requirements, as for example for capsule systems which are particularly stable in an acidic medium, the aqueous solutions of alkali metals from main groups 1 and 2 of the Periodic Table of the Elements are more particularly suitable.

In the context of the method of the invention, at the beginning of the reaction (method step a)) of the amine and/or aromatic alcohol with the aldehydic component, stirring may be carried out, in which case the stirring speed can be 500 to 2500 rpm, more particularly 1000 to 2000 rpm. To the resulting mixture it is then possible to add at least one copolymer which comprises units of AMPS and/or AMPP and one or more (meth)acrylate monomers, and the substance to be encapsulated. Preferably, later, and in particular immediately before or during the raising of the alkalinity (method step b), the stirring speed is increased, and may then be 3000 to 5000 rpm, more particularly 3500 to 4500 rpm, especially 4000 rpm.

The stirring speed increased in this way is preferably maintained until the viscosity values of the mixture fall, the stirring speed being lowered after the onset of a viscosity decrease, preferably to 500 to 2500 rpm, more preferably to 1000 to 2000 rpm. An earlier lowering of the stirring speed may lead likewise to the unwanted gelling of the batch.

Preferably, after the beginning of the described decrease in viscosity, stirring is continued for at least 20 minutes, more particularly between 30 and 180 minutes, preferably at a stirring speed of 1000 to 2000 rpm and at a temperature of 40 to 65° C., before, in step c) of the method, the capsules are cured by temperature increase. This phase, after the beginning of the described viscosity decrease and before the curing of the capsules, is also referred to in the present invention as the rest phase. The rest phase may be used preferably in order to achieve the preformation of sufficiently stable capsule walls—in other words, to form the capsule walls with sufficient stability that core material no longer escapes.

The microcapsules of the invention are preferably formaldehyde-free. They can be processed as stable core/shell microcapsules from the aqueous slurry to form a dry, free-flowable powder.

The microcapsules may be given a charge of hydrophobic and hydrophilic materials, with gaseous, liquid, and solid substances.

The present invention further provides for the use of microcapsules or microcapsule dispersions of the invention for the controlled release of core materials, which may be hydrophilic (e.g., flavors) or hydrophobic. The core materials are, for example, active ingredients, preferably selected from the group of the fragrances and flavors, pesticides, herbicides, lubricants, glidants (e.g., fluorinated hydrocarbons), insecticides, active antimicrobial ingredients, active pharmaceutical ingredients, active cosmetic ingredients (e.g., for shampoo), latent heat storage materials (e.g., waxes), catalysts (e.g., organic carbonates), self-healing agents (e.g., norbornene, dicyclopentadiene), coating systems such as varnishes (e.g., fragrance varnishes), colors (e.g., for carbonless copy systems), hydrophobic waxes, hydrophobic ene components or hydrophobic solvents.

Also provided by the present invention are products which comprise microcapsules or microcapsule dispersions of the invention, and whose use lies preferably in an area of application selected from the fields of coatings, such as carbonless copy systems, coating and impregnation of papers and security feature coating, catalyst-filled microcapsules, paint technology such as paint manufacture, construction chemicals, dental technology, preferably as an ingredient of fast-curing dental filling compositions, self-healing systems, cosmetics, preferably for fragrance and flavor oils, pharmacy, preferably as vehicles for active ingredients, medical technology, as for example for the encapsulation of species emitted by neurotransmitters such as NO, such as of nitroglycerol, for example, laundering, cleaning, disinfecting, adhesively bonding, flame suppression, the treatment of plants, preferably as fungicide, pesticide, insecticide or herbicide, or corrosion control.

The microcapsules of the invention can be used, for example, for producing varnishes, such as for fragrance varnishes, for example, and can be employed variably in terms of their degree of crosslinking, their size, their wall thickness and surface finish, and also in terms of the core material.

On account of the high chemical and physical resistance, they are suitable as stable core/shell capsule systems, including for use in aggressive media. Hence it is possible to produce fragrance varnishes which can be applied via conventional doctor-blade systems in the coat thicknesses known in the printing industry, without a notable proportion of the capsules being destroyed.

The microcapsules generally have an average diameter of 1-1000 μm the context of the present invention, the term "microcapsule" also encompasses nanocapsules, i.e., capsules having an average diameter <1 μm. The capsules preferably have an average diameter of 0.1 to 100 μm. The wall thickness is adjustable and may be 0.01-100 μm, more particularly, for example, 0.1 to 10 μm.

Also possible is the production of solid spheres, in other words particles which do not surround a core material. These solid spheres may have an average diameter of below 500 nm (preferably between 300 and 400 nm). They may preferably be monodisperse solid spheres. Phloroglucinol can be used in one embodiment for producing these solid spheres.

The solid spheres of the invention may find use as a standard or control means in, for example, medical technology (e.g., as a calibrating solution in particle sizers or erythrocyte counters), or may be utilized as an abrasive ingredient in abrasives, for decorative effects or as spacers for printable varnishes with pressure-sensitive particles.

The microcapsules of the invention can be used in the form of aqueous dispersions as impregnating resins in the wood/material segment, and are suitable more particularly as impregnating resins with additional functions such as catalytic effects, color effects, thermochromic effects or security effects for decorative coating systems.

The present invention is elucidated below by a number of working examples, which are purely illustrative in nature and do not restrict the invention in any way:

Example 1

Preparation of Copolymers

AMPS-hydroxybutyl acrylate

For the 1500 g batch, 891 g of demineralized water are introduced together with 585 g of AMPS (50% aqueous solution) and 7.5 g of 4-hydroxybutyl acrylate (HBA) into the reactor and placed under an inert gas atmosphere. The reaction mixture is heated to 75° C. with stirring (400 rpm). Of the water-soluble initiator sodium peroxodisulfate, 0.03 g is dissolved in 15 g of water and injected into the reactor using a syringe when the reaction temperature has been attained. Following attainment of the maximum temperature, an hour of after-reaction begins. The batch is subsequently cooled to room temperature and admixed with 1.5 g of preservative.

The aqueous solution is characterized by the viscosity, solids content, and pH. The viscosity is 540 mPas (measured at 20 rpm Brookfield), the solids content is 21%, and the pH is 3.3. 3 g of copolymer are applied to a Petri dish and dried in a drying cabinet at 160° C. for 24 hours. The final mass is 0.69 g, corresponding to a yield of 21.6%.

AMPS-polyalkylene glycol monomethacrylate

The initial charge consists of 912 g of demineralized water, 240 g of AMPS, and 7.5 g of poly(ethylene/propylene) glycol monomethacrylate (Bisomer PEM63PHD from Cognis, CAS No. 589-75-9). The mixture is placed under an inert gas atmosphere. The reaction mixture is heated to 75° C. with stirring (400 rpm). 1.5 g of sodium peroxodisulfate are dissolved in 15 g of water and transferred into the reactor using a syringe. When the temperature in the reactor has attained a maximum and is beginning to fall, 240 g of AMPS with 83 g of PEM63PHD are metered in over a period of an hour using a peristaltic pump. This is followed by a half-hour after-reaction. The batch is subsequently cooled to room temperature and admixed with 1.5 g of preservative.

The aqueous solution is characterized by the viscosity, solids content, and pH. The viscosity is 110 mPas (measured at 20 rpm Brookfield), the solids content is 23%, and the pH is 3.1. 3 g of copolymer are applied to a Petri dish and dried in a drying cabinet at 160° C. for 24 hours. The final mass is 0.68 g, corresponding to a yield of 21.6%.

Example 2

Phloroglucinol-melamine Microcapsules

Preparation of the Precondensate 5.4 g of phloroglucinol and 0.6 g of melamine are dissolved in 78.6 g of distilled water. The pH is adjusted to 3 using 1.2 g of 85% strength formic acid. The mixture is heated to 35° C. and 14.2 g of 50% strength glutaraldehyde solution are added. After 5 minutes the soluble precondensate begins to form, evident from the dissolution of the melamine and phloroglucinol, which is barely soluble in water. The overall solids content of the precondensate is 14.0% by weight.

Production of the Microcapsules 41.5 g of the soluble precondensate obtained in stage a) are admixed after 5 minutes with 3.0 g of the protective colloid, a copolymer of AMPS (2-acrylamido-2-methyl-1-propylsulfonic acid) and PEM 6 (polyethylene glycol monomethacrylate), and 23.7 g of a fragrance oil for encapsulation. For the formation of particles, the speed is increased from 500 rpm to 2500 rpm at the same time. After 20 minutes, the resin begins to cure to form structured capsule walls. In the following hour, stirring takes place at a rotation speed of 600 rpm. Within this hour, after 15 minutes, 7.5 g of a 14% by weight phloroglucinol slurry, acidified to a pH of 3 using formic acid (85%), are metered in for 45 minutes, and also, after 20 minutes, 16 g of water are added, in order to prevent the slurry thickening. This is followed by a 2-hour curing phase at 80° C. Subsequently, 4.2 g of a 33% by weight melamine slurry (Folco slurry) acidified with 85% formic acid is metered in for 30 min. This is followed, lastly, by after-curing at a pH of 3 for 30 min. The capsule slurry is cooled to room temperature and adjusted to a pH of 7 using aqueous sodium hydroxide solution.

Technical data of the microcapsules obtained:
Diameter D(90): 10 μm
Solids: 33%
Core fraction: 70%
Efficiency: 90%
Powder yield: 90%
Residual aldehyde
content: <500 ppm, determined by GC (FT-IR)

Example 3

Melamine Microcapsules 31.0 g of glutaraldehyde solution (50%) are heated to 55° C. with 90 g of distilled water, and a pH of 9.2 is set using aqueous sodium hydroxide solution (10%). Subsequently 5.6 g of melamine are added and this mixture is precondensed at 55° C. for 10 minutes. Still at 55° C., 9.5 g of copolymer of AMPS (2-acrylamido-2-methyl-1-propanesulfonic acid) and PEM 6 (polyethylene glycol monomethacrylate) and also 78 g of diethyl phthalate are added, and the speed is increased to 1600 rpm. Then amidosulfonic acid (15%) is added to lower the pH to 6.1. After about 2 minutes, a stable capsule size of around 30 μm established. At a lower speed (800 rpm), the capsules are cured at 55° C. for 1 h and 80° C. for 3 h. In the course of the curing, 4 g of melamine are added to the batch, and in the last hour of curing the pH is held at 9-11 by means of aqueous sodium hydroxide solution (20%).

Technical data of the microcapsules obtained:
Diameter D(90): 28 μm
Solids: 46.4%
Core fraction: 74.8%
Efficiency: 97%
Powder yield: 50%
Residual aldehyde
content: <500 ppm, determined by GC (FT-IR)

Example 4

General Synthesis Instructions for Terpolymers 495.0 g of monomer 1 (AMPS or AMPP) and 7.5 g of monomer 2 (meth/acrylate monomer) and 898 g of demineralized water are transferred as an initial charge into a double-wall glass reactor. The initial charge is briefly mixed and then gassed with argon for 10 minutes. The reaction mixture is subsequently heated to 75° C. and started with an initiator solution (0.75 g in 15 g of water). When the maximum temperature has been reached in the reactor, monomer 2 (37.5 g) and monomer 3 (third monomer) (15 g) are metered in over the course of an hour using a peristaltic pump or a syringe pump. Following the metered addition, there is an hour of after-reaction, after which the aqueous polymer solution obtained is cooled. When the temperature in the reactor is below 40° C., 1.5 g of preservative are added, and the homogeneous product is discharged.

Example 5

AMPS-polyalkylene glycol monomethacrylate-N-vinylcaprolactam

The initial charge consists of 883 g of demineralized water, 525 g of AMPS, 7.5 g of PEM63PHD, and 15 g of N-vinylcaprolactam. The mixture is placed under an inert gas atmosphere and is heated to 75° C. with stirring (250 rpm). 0.75 g of sodium peroxodisulfate is dissolved in 15 g of water and injected into the reactor using a syringe. When the temperature has reached a maximum and is beginning to fall, 15 g of N-vinylcaprolactam with 37.5 g of PEM63PHD are metered in over a period of one hour using a syringe pump. This is followed by a half-hour after-reaction. Thereafter the batch is cooled to room temperature and admixed with 1.5 g of preservative.

The aqueous solution is characterized by the viscosity, solids content, and pH. The viscosity is 1800 mPas (measured at 20 rpm Brookfield), the solids content is 22.1%, and the pH is 3.5. 3 g of terpolymer are applied to a Petri dish and dried in a drying cabinet at 160° C. for 24 hours. The final mass is 0.67 g and corresponds to a yield of 22.3%.

The invention claimed is:

1. Microcapsules whose capsule walls comprise a resin which is obtained by reacting
   a) at least one compound selected from the group consisting of
      a1) amines, and
      a2) aromatic or heteroaromatic compounds which are unsubstituted or substituted by one or more substituents selected from the group consisting of $C_1$-$C_{20}$ alkyl, OH, OR, COOH, SH, SR, NHCOR, OCOR, halogen and aromatic, where R represents a $C_1$-$C_{10}$ alkyl group,
   with,
   b) at least one aldehydic component which has at least two C atoms per molecule, in the presence of
   c) at least one copolymer which comprises units of 2-acrylamido-2-methylpropanesulfonic acid or its salts (AMPS) and/or 2-acrylamido-2-methylpropanephosphonic acid or its salts (AMPP) and units of one or more (meth)acrylates,
   wherein, the use of formaldehyde is excluded.

2. The microcapsules as claimed in claim 1, wherein one or more amines having at least two amine groups per molecule are selected as component a).

3. The microcapsules as claimed in claim 1, wherein one or more compounds selected from the group consisting of ureas, melamines, and benzoguanamines are selected as component a).

4. The microcapsules as claimed in claim 1, wherein one or more aromatic or heteroaromatic alcohols and/or one or more aromatic or heteroaromatic carboxylic acids are selected as component a).

5. The microcapsules as claimed in claim 4, wherein the at least one aromatic alcohol has at least two aromatically attached free hydroxyl groups per molecule.

6. The microcapsules as claimed in claim 4, wherein the at least one aromatic alcohol is a phenol having two or more hydroxyl groups.

7. The microcapsules as claimed in claim 6, wherein the alcohols are present in the form of their salts, ethers or esters and the carboxylic acids are present in the form of their salts or esters.

8. The microcapsules as claimed in claim 6, wherein the at least one aromatic alcohol is selected from the group consisting of pyrocatechol, resorcinol, hydroquinone, 1,4-naphthohydroquinone, phloroglucinol, pyrogallol, and hydroxyhydroquinone.

9. The microcapsules as claimed in claim 8, wherein the at least one aromatic alcohol is selected from the group consisting of resorcinol and phloroglucinol.

10. The microcapsules as claimed in claim 1, wherein an aromatic alcohol or ether thereof or derivative thereof is selected as component a).

11. A microcapsule as claimed in claim 1, wherein component a) comprises a mixture of a1) one or more amines, and a2) one or more aromatic or heteroaromatic alcohols and/or one or more aromatic or heteroaromatic carboxylic acids.

12. The microcapsules as claimed in claim 1, wherein the aldehydic component b) is selected from the group consisting of aliphatic and aromatic aldehydes.

13. The microcapsules as claimed in claim 12, wherein the aldehydic component is selected from valeraldehyde, caproaldehyde, caprylaldehyde, decanal, succinaldehyde, cyclohexanecarbaldehyde, cyclopentanecarbaldehyde, 2-methyl-1-propanal, 2-methylpropionaldehyde, acetaldehyde, acrolein, aldosterone, antimycin A, 8'-apo-β-caroten-8'-al, benzaldehyde, butanal, chloral, citral, citronellal, crotonaldehyde, dimethylaminobenzaldehyde, folic acid, fosmidomycin, furfural, glutaraldehyde, glyceraldehyde, glycolaldehyde, glyoxal, glyoxylic acid, heptanal, 2-hydroxybenzaldehyde, 3-hydroxybutanal, hydroxymethylfurfural, 4-hydroxynonenal, isobutanal, isobutyraldehyde, methacrolein, 2-methylundecanal, mucochloric acid, N-methylformamide, 2-nitrobenzaldehyde, nonanal, octanal, oleocanthal, orlistat, pentanal, phenylethanal, phycocyanin, piperonal, propanal, propenal, protocatechualdehyde, retinal, salicylaldehyde, secologanin, streptomycin, strophanthidin, tylosin, vanillin, and cinnamaldehyde.

14. The microcapsules as claimed in claim 13, wherein the aldehydic component is selected from the group consisting of glutaraldehyde and succinaldehyde.

15. The microcapsules as claimed in claim 1, wherein the at least one aldehydic component has at least two free aldehyde groups per molecule.

16. The microcapsules as claimed in claim 1, wherein the copolymer is a bipolymer or a terpolymer.

17. The microcapsules as claimed in claim 1, wherein the copolymer c) is constructed from units of AMPS or AMPP and one or more (meth)acrylates.

18. The microcapsules as claimed in claim 17, wherein the (meth)acrylates in copolymer c) are selected from the group consisting of a) 4-hydroxybutyl acrylate

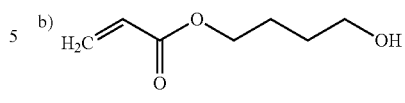

HBA 2-hydroxypropyl methacrylate

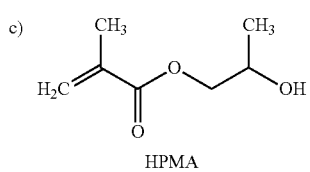

HPMA ammonium sulfatoethyl methacrylate

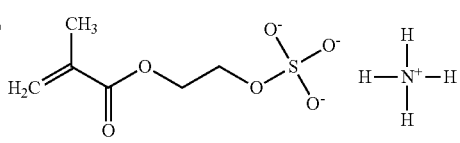

SEM pentapropylene glycol methacrylate

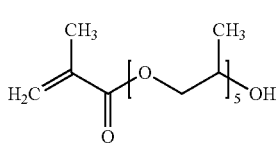

PPM 5 Li acrylic acid

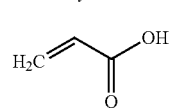

AS hexaethylene glycol methacrylate

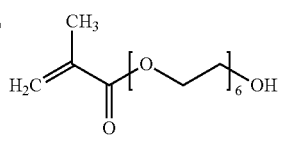

PEM 6 LD hexapropylene glycol acrylate

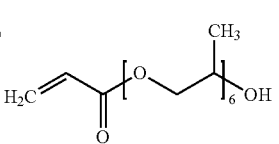

PPA 6 hexaethylene glycol acrylate

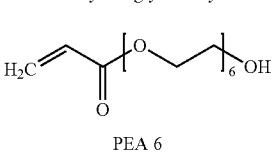

PEA 6 hydroxyethyl methacrylate

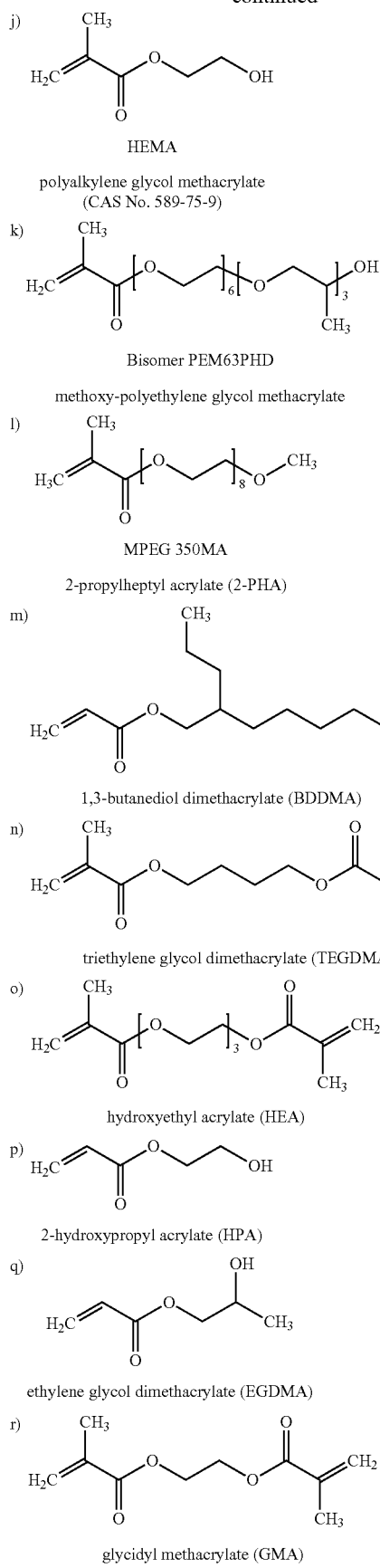
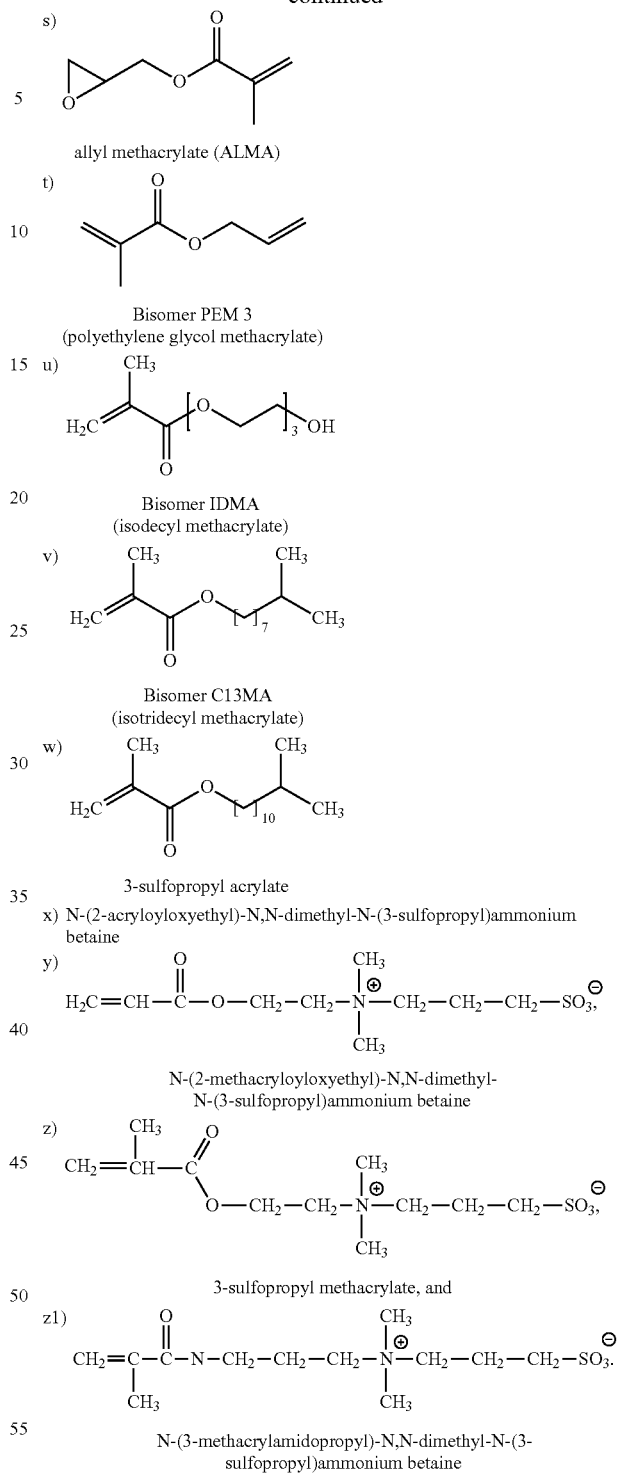

19. The microcapsules as claimed in claim 17, wherein the copolymer c) comprises one or more further monomers selected from the group consisting of vinyl compounds, unsaturated dicarboxylic or polycarboxylic acids, and the salts of amyl compounds or allyl compounds.

20. The microcapsules as claimed in claim 17, wherein the copolymer c) is constructed from AMPS and one or more (meth)acrylates.

21. The microcapsules as claimed in claim 1, wherein the molar ratio of the at least one component a) to the at least one aldehydic component b) is between 1:1 and 1:5.

22. The microcapsules as claimed in claim 1, wherein the capsule surface is aftertreated with a nitrogen-containing agent, an oxygen-containing agent or a silicon-containing agent, with a silica gel, or with aromatic alcohol a).

23. The microcapsules as claimed in claim 1, wherein at least one core material is enclosed in the capsule.

24. The microcapsules as claimed in claim 1, wherein the capsule is formaldehyde-free.

25. A microcapsule dispersion comprising one or more microcapsules as claimed in claim 1.

26. A method of using microcapsules as claimed in claim 1 for the release of hydrophilic or hydrophobic active ingredients selected from the group consisting of fragrances, flavors, colors, latent heat storage materials, solvents, catalysts, coating systems, reactive (meth)acrylates, ene components, active antimicrobial ingredients, lubricants, glidants, active pharmaceutical ingredients, active cosmetic ingredients, self-healing agents, waxes, and pesticides, the method comprising:

providing microcapsules as claimed in claim 1 containing the hydrophilic or hydrophobic active ingredients; and using the microcapsules to release the hydrophilic or hydrophobic active ingredients.

27. Products comprising microcapsules as claimed in claim 1.

28. A method of using the products as claimed in claim 27 in at least one area of application selected from the fields of coatings, paint technology, construction chemicals, catalyst technology, corrosion control, dental technology, self-healing systems, cosmetics, pharmacy, laundering, cleaning, disinfecting, adhesive bonding, treatment of plants, as a fungicide, a pesticide, an insecticide, a herbicide, or in medical technology, the method comprising:

providing products comprising microcapsules as claimed in claim 1; and using the products in at least one area of application selected from the fields of coatings, paint technology, construction chemicals, catalyst technology, corrosion control, dental technology, self-healing systems, cosmetics, pharmacy, laundering, cleaning, disinfecting, adhesive bonding, treatment of plants, as a fungicide, a pesticide, an insecticide, a herbicide, or in medical technology.

* * * * *